United States Patent [19]

Sorenson et al.

[11] Patent Number: 4,457,311

[45] Date of Patent: Jul. 3, 1984

[54] ULTRASOUND IMAGING SYSTEM FOR SCANNING THE HUMAN BACK

[75] Inventors: Paul D. Sorenson, Blaine; Dale A. Dickson, Fridley, both of Minn.

[73] Assignee: Medtronic, Inc., Minneapolis, Minn.

[21] Appl. No.: 414,705

[22] Filed: Sep. 3, 1982

[51] Int. Cl.³ .......................................... A61B 10/00
[52] U.S. Cl. ..................................... 128/660; 73/625
[58] Field of Search ............................. 128/660–661, 128/736, 781; 73/618–626, 633–638, 640–641

[56] References Cited

U.S. PATENT DOCUMENTS

| | | | |
|---|---|---|---|
| 4,094,306 | 6/1978 | Kossoff | 128/660 X |
| 4,209,022 | 6/1980 | Dory | 73/626 X |
| 4,213,183 | 7/1980 | Barron et al. | 73/634 X |
| 4,233,988 | 11/1980 | Dick et al. | 128/660 |
| 4,240,295 | 12/1980 | Uranishi | 128/660 X |
| 4,242,912 | 1/1981 | Burckhardt et al. | 73/626 |
| 4,245,250 | 1/1981 | Tiemann | 358/140 |
| 4,246,791 | 1/1981 | Glenn | 73/620 |
| 4,252,026 | 2/1981 | Robinson | 73/626 |
| 4,253,338 | 3/1981 | Iinuma et al. | 73/626 |
| 4,265,121 | 5/1981 | Cribbs | 73/607 |
| 4,271,706 | 6/1981 | Ledley | 73/614 |
| 4,271,842 | 6/1981 | Specht et al. | 128/661 |
| 4,272,991 | 6/1981 | Cribbs | 73/621 |

OTHER PUBLICATIONS

"Other Ultrasonic Investigations" by Wells, P. N. T., Ultrasonics in Clinical Diagnosis, pp. 152–153, Churchill Livingstone, N.Y. 1977.

Primary Examiner—Kyle L. Howell
Assistant Examiner—Francis J. Jaworski
Attorney, Agent, or Firm—Robert J. Klepinski; John L. Rooney; Joseph F. Breimayer

[57] ABSTRACT

An ultrasound scanning system having a linear array of ultrasound transducers and a transporter system for moving the transducers along the human back. There is a means for producing a position signal indicative of the position of the array along the plane of the back, and a means for producing a range signal representative of the distance of objects interacting with the ultrasound signal from the transducer. An output means, such as a printer or cathode ray tube display, is responsive to the range signal and the position signal to produce an output representative of the structure of the body imaged during the back scan.

4 Claims, 25 Drawing Figures

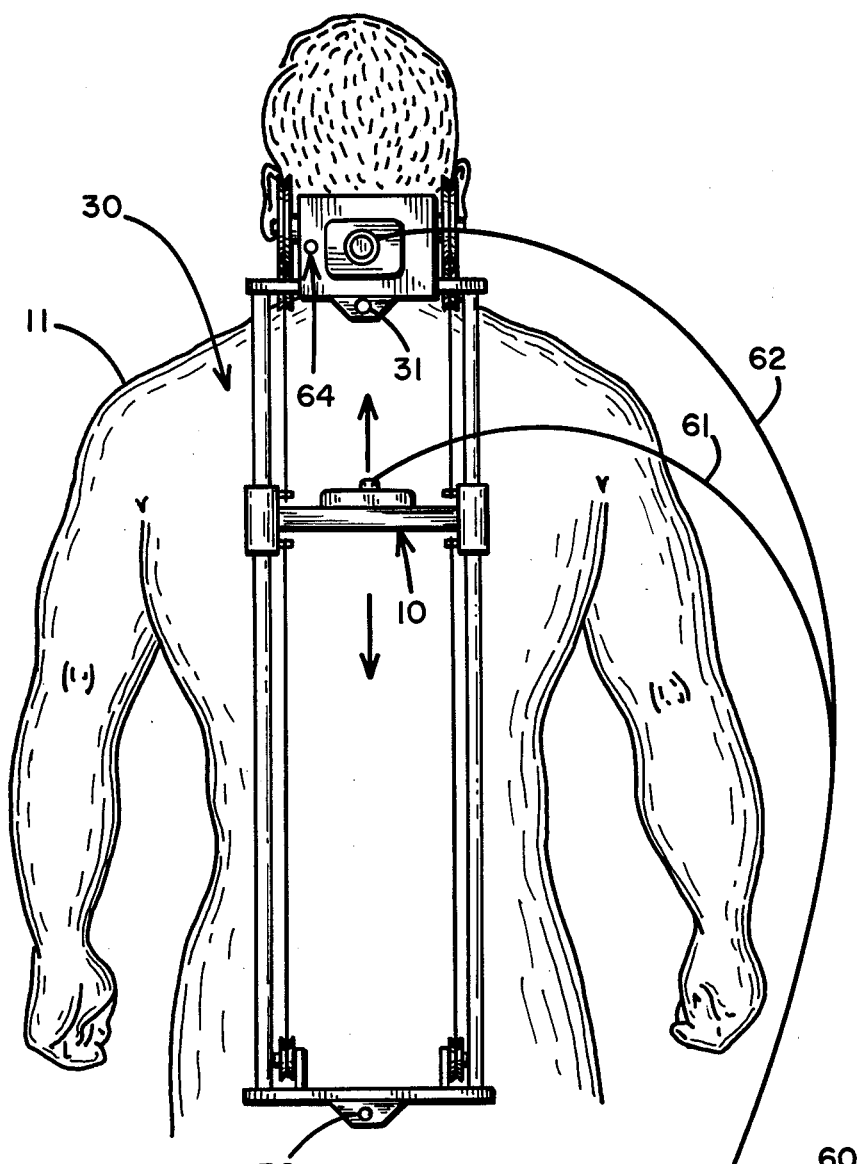
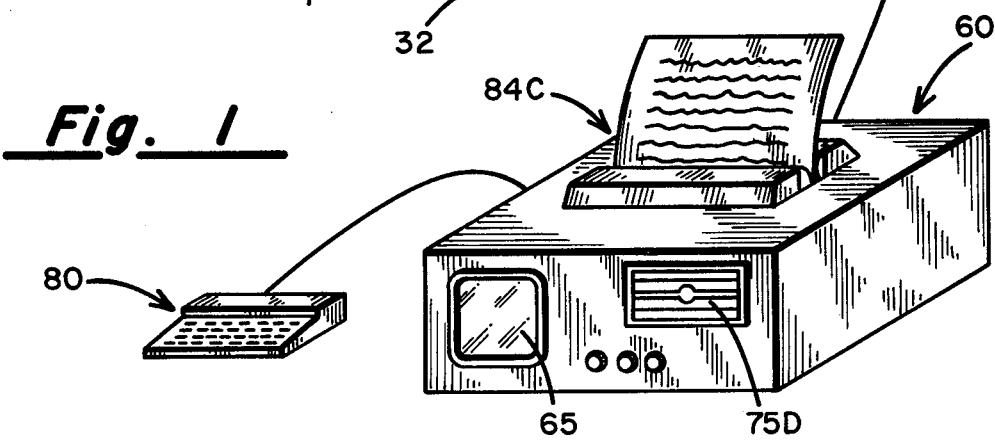
Fig. 1

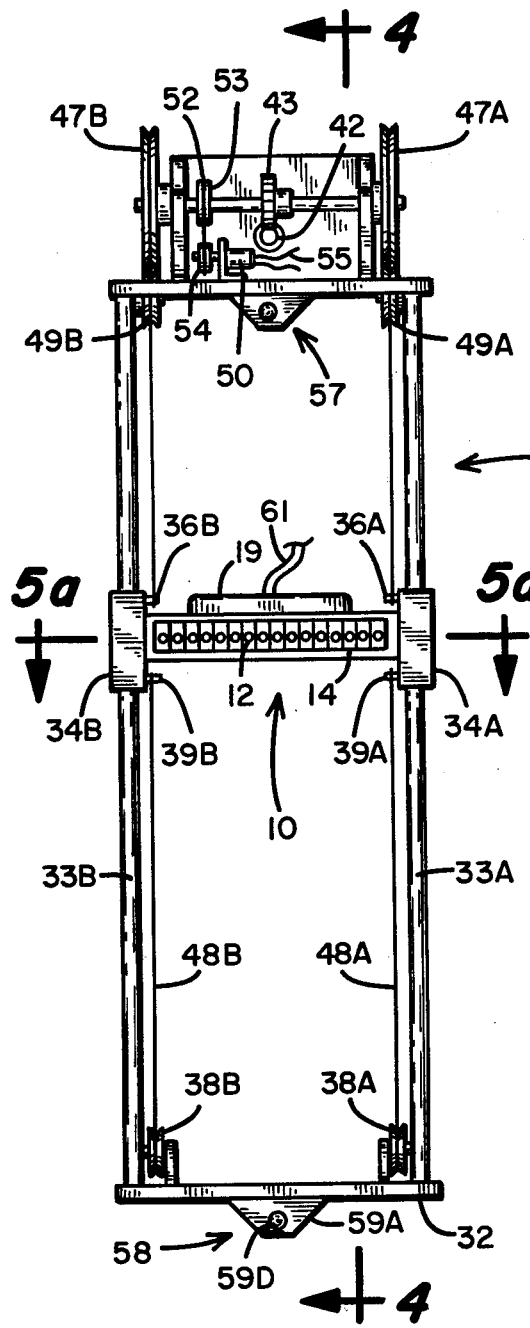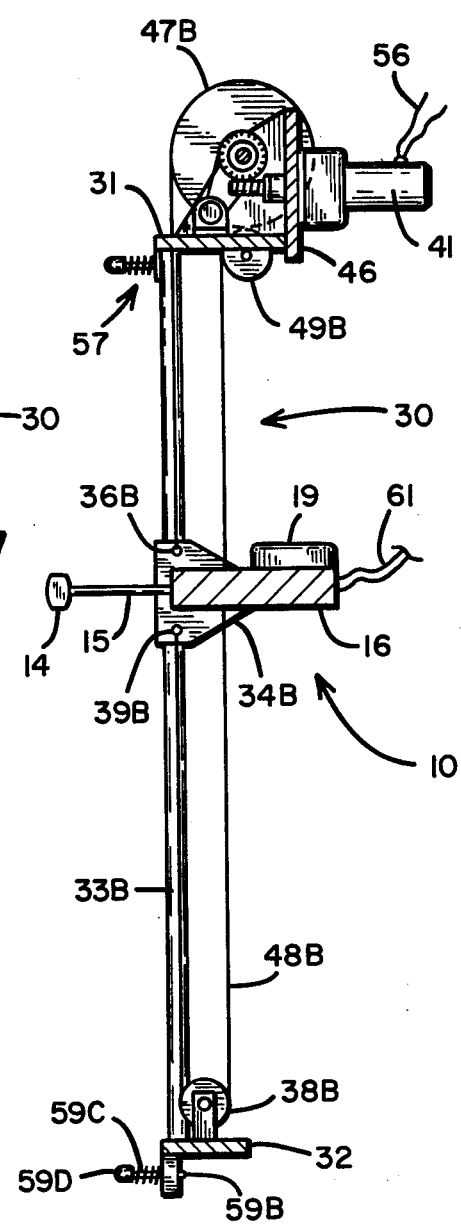
Fig. 3
Fig. 4

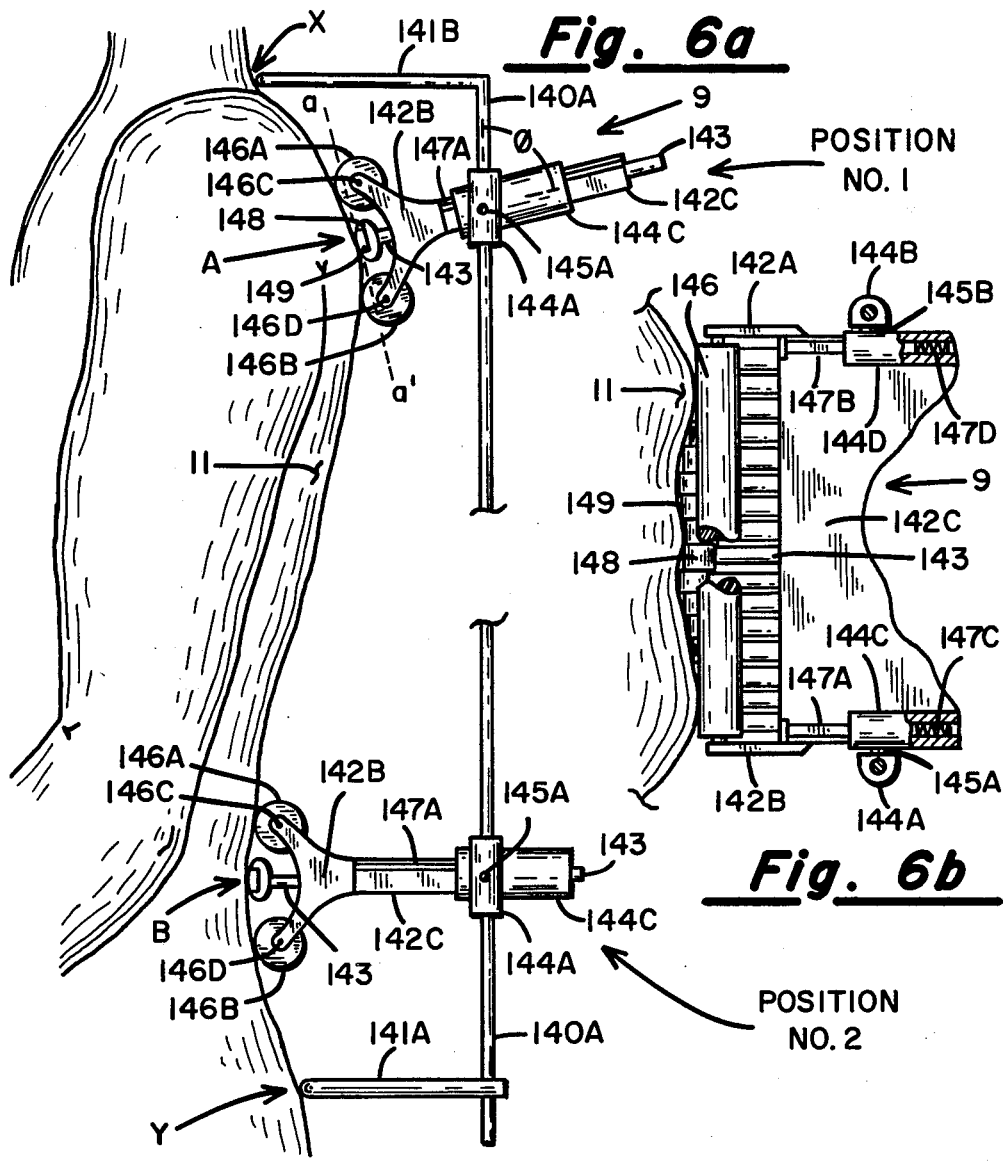

POSITION A/D CONVERTER

MOTOR CONTROL

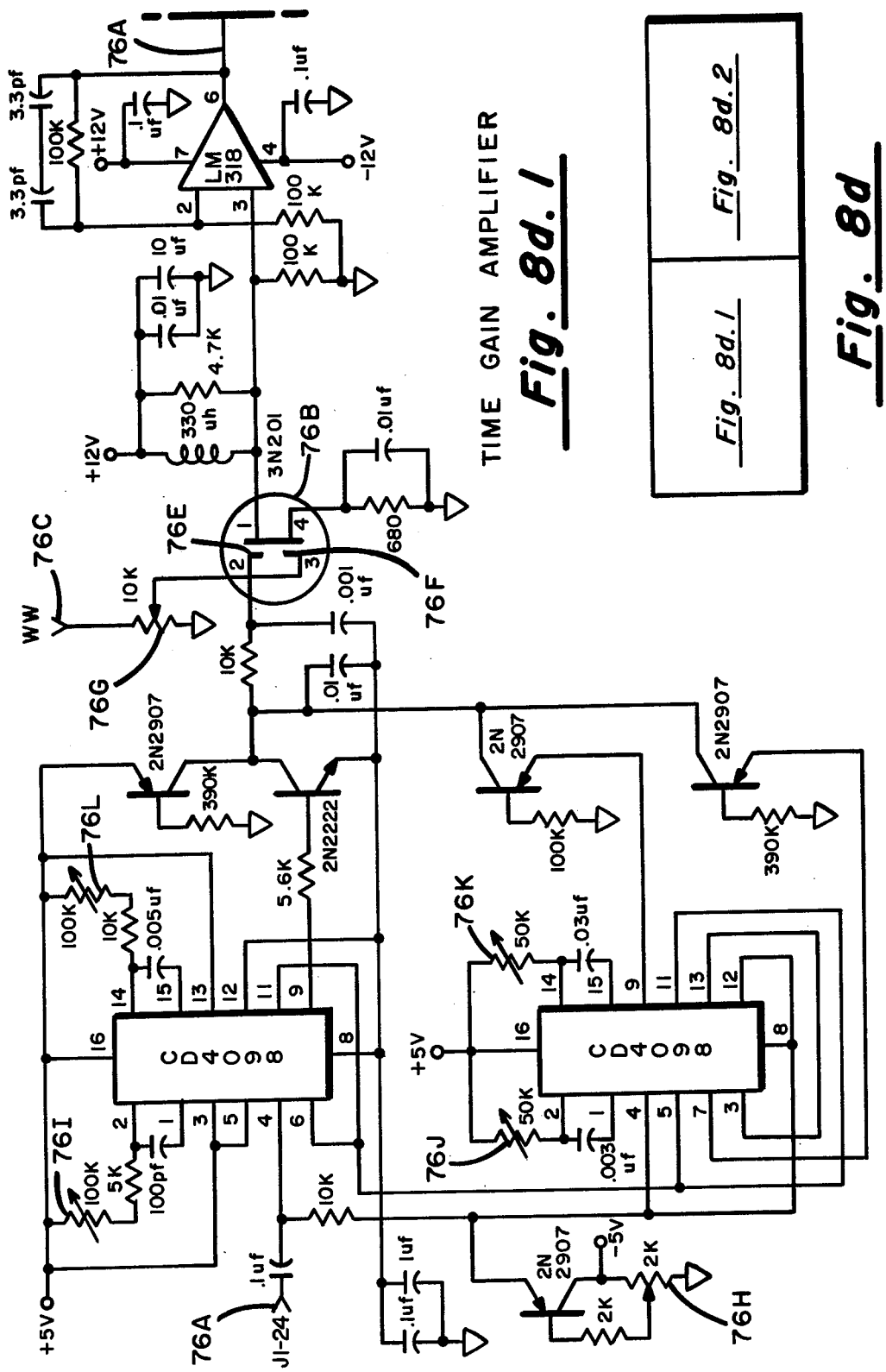

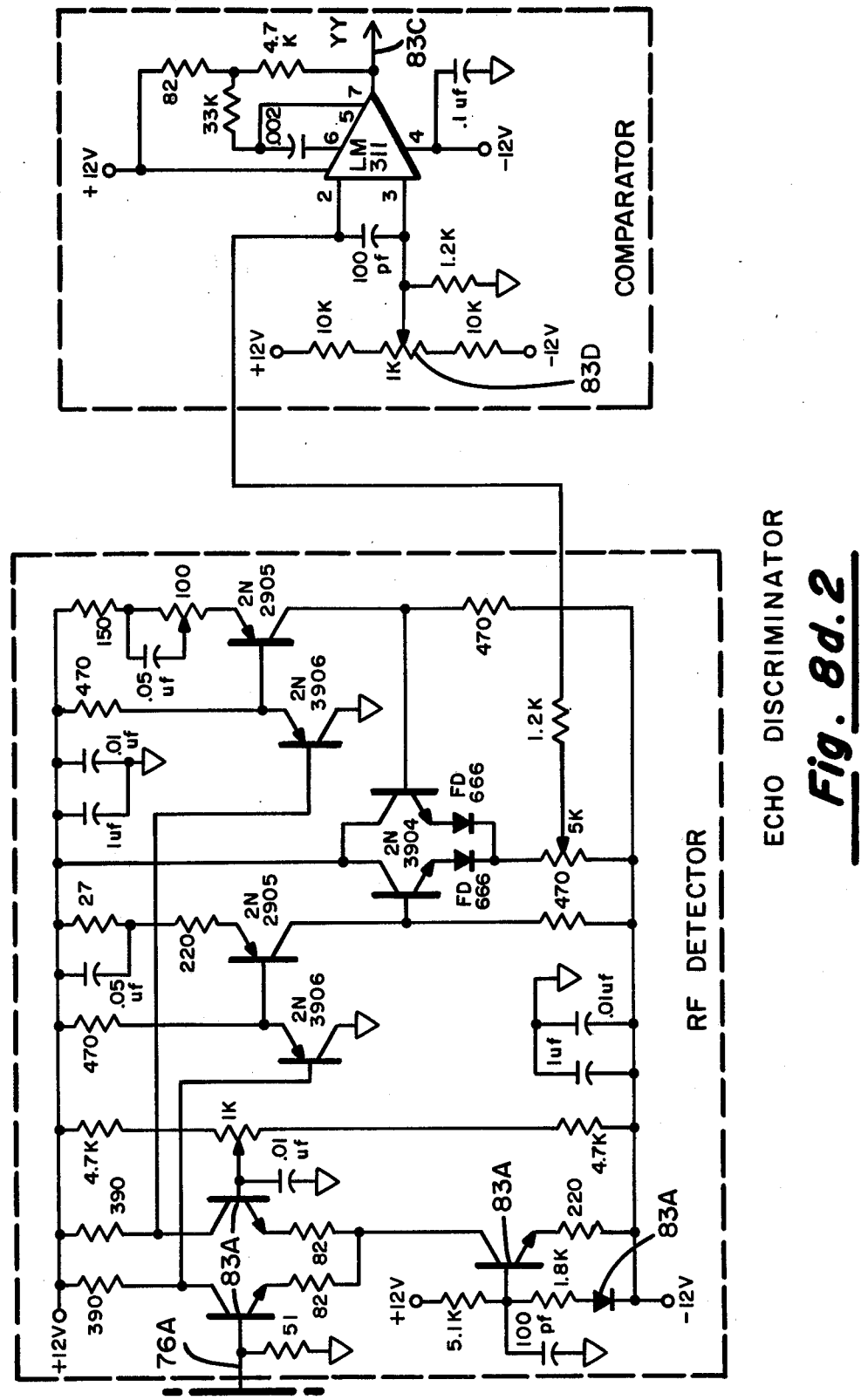
Fig. 8d.2

RANGE COUNTER #1

RANGE COUNTER #2

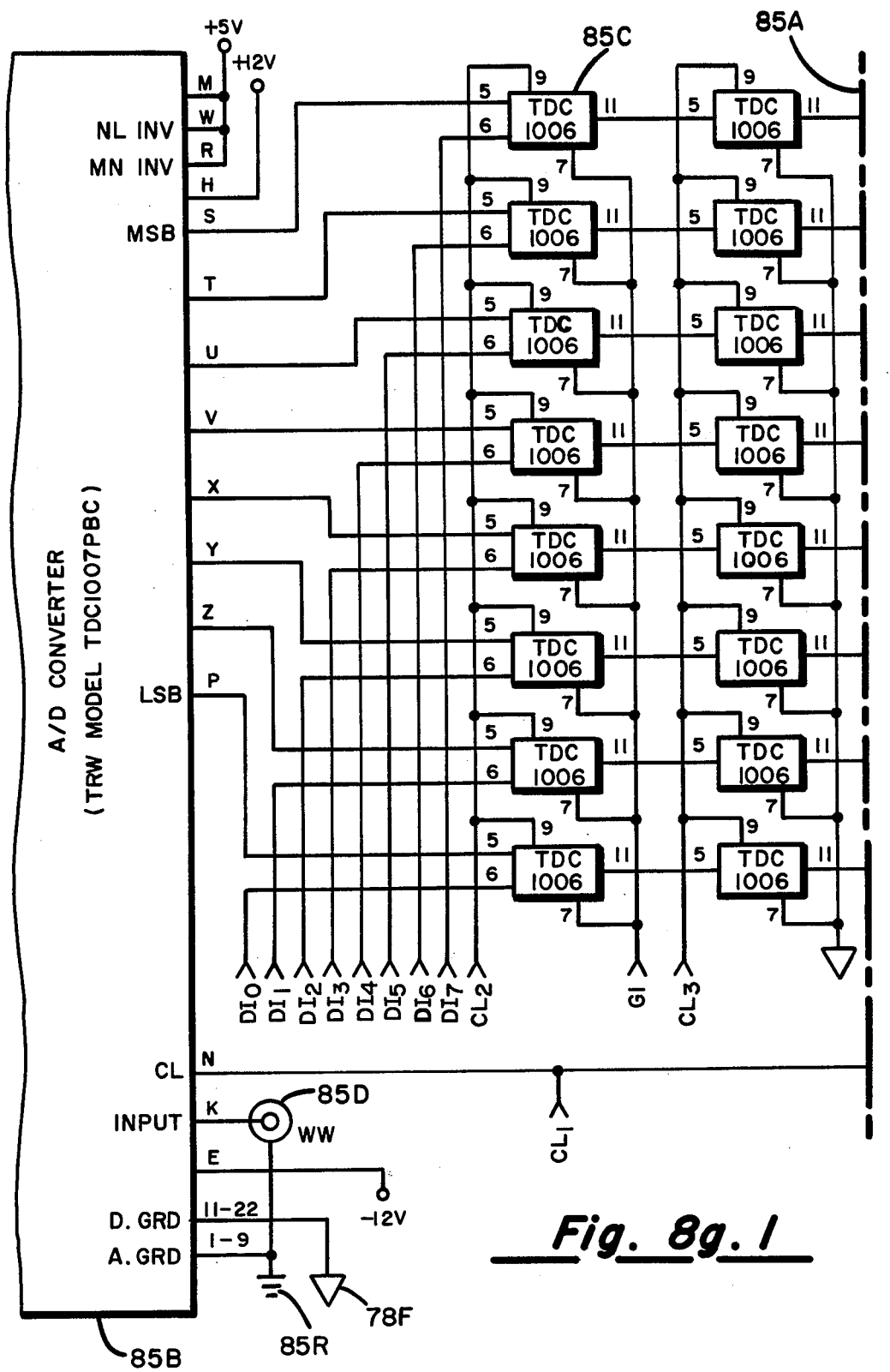
Fig. 8g.1

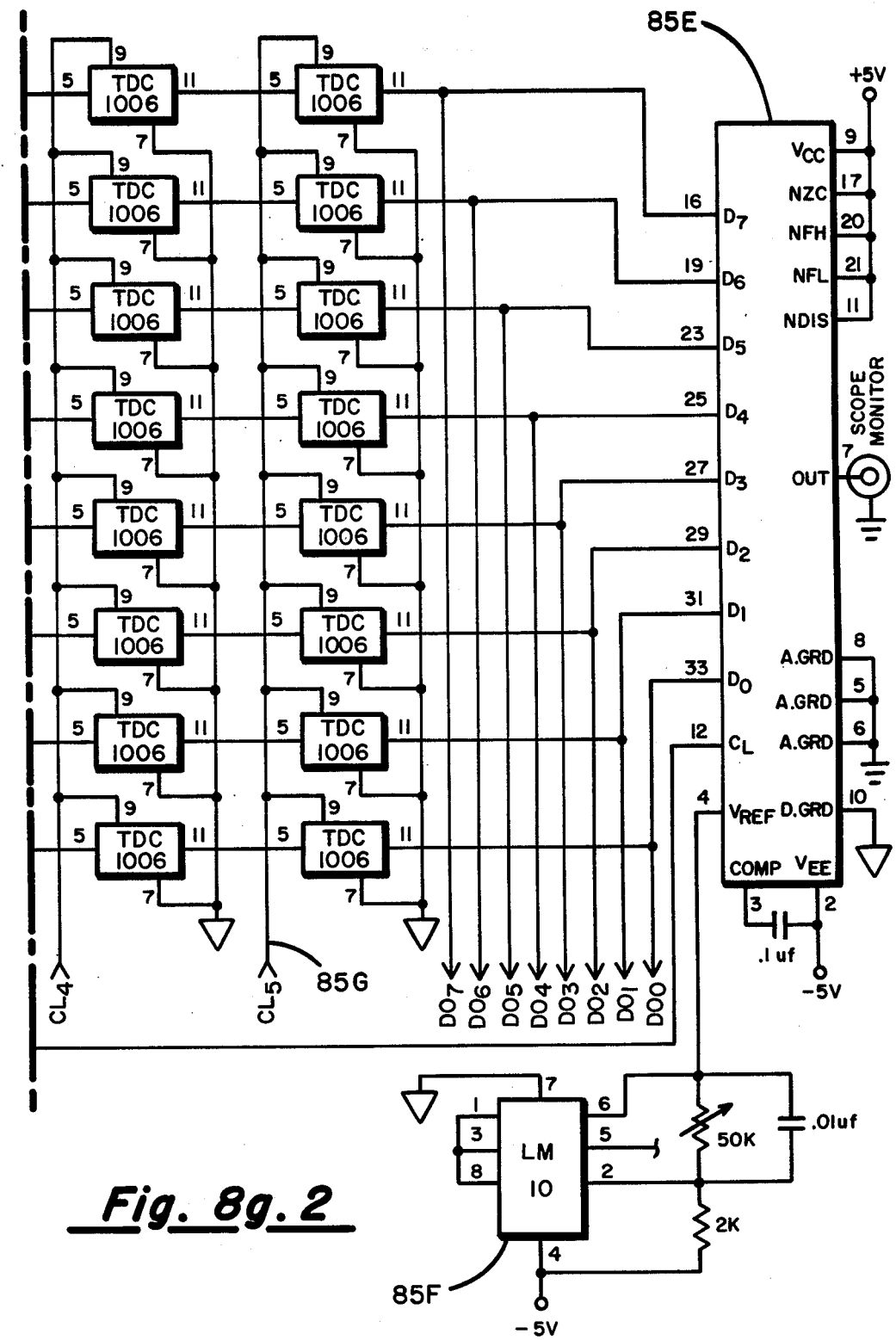
Fig. 8g.2

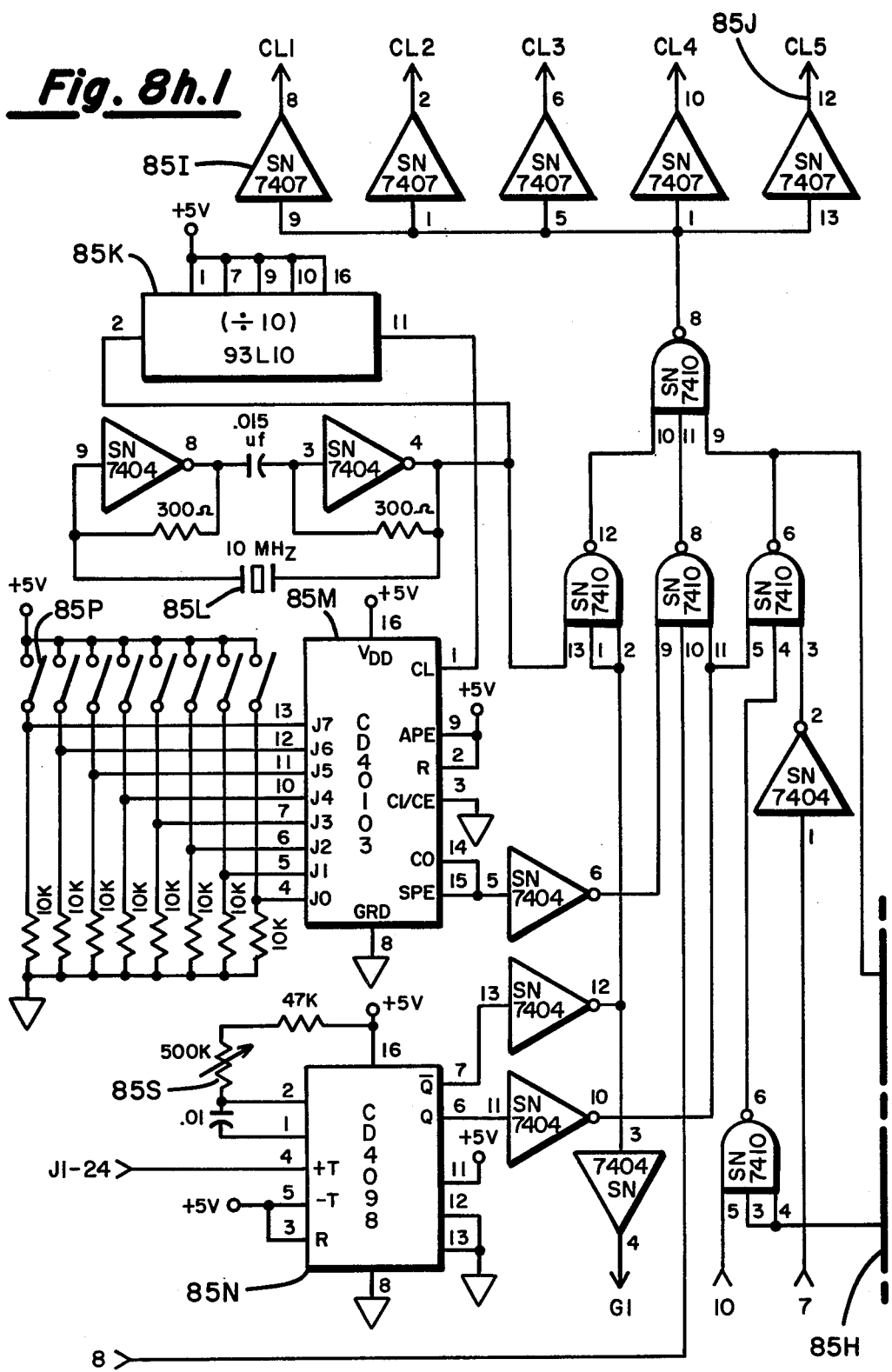
Fig. 8h.1

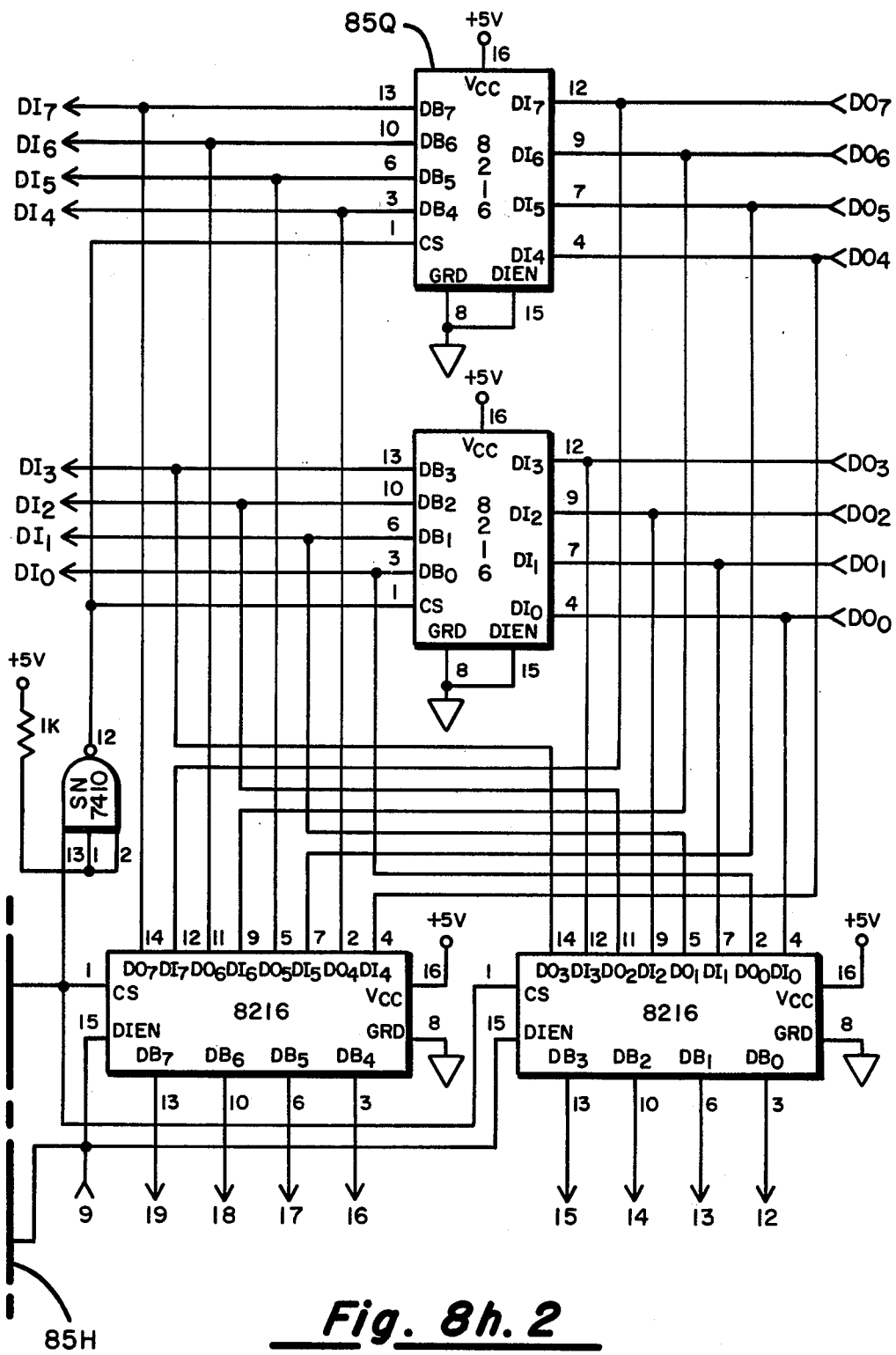
Fig. 8h.2

ULTRASOUND IMAGING SYSTEM FOR SCANNING THE HUMAN BACK

REFERENCES TO COPENDING APPLICATIONS

This application contains matter disclosed and claimed in the following copending applications filed on even date with the present application:
ULTRASOUND SCANNING SYSTEM FOR SKELETAL IMAGING, Ser. No. 415,042, by Paul D. Sorenson, Dale A. Dickson, Larry A. McNichols, and John D. Badzinski;
ULTRASOUND SCANNER WITH MAPPED DATA STORAGE, Ser. No. 415,044, by Paul D. Sorenson and John D. Badzinski;
SYSTEM WITH SEMI-INDEPENDENT TRANSDUCER ARRAY, Ser. No. 414,704, by Paul D. Sorenson and Dale A. Dickson; and
ULTRASOUND IMAGING SYSTEM, Ser. No. 415,043, by Paul D. Sorenson and Larry A. McNichols.

BACKGROUND OF THE INVENTION

1. Field of the Invention

This invention in general relates to the field of ultrasound imaging, and more particularly concerns a system and method for ultrasound imaging of structures of the human back, such as the spinal column and ribs, which lends itself to the diagnosis of scoliosis.

2. Description of the Prior Art

Scoliosis is a disease resulting in the deformity of the spine. The disorder, which is a significant worldwide health problem, is characterized by both lateral curvature and rotation of the vertebrae. The cause of idiopathic scoliosis, which is the most common class of scoliosis, is unknown, but the symptoms generally appear during the developmental years. Failure to effectively treat the disorder in those cases where the curvature progressively grows worse leads to deformity of the torso and potentially, cardiopulmonary distress. Patients are often treated by orthopedic surgeons during the adolescent years of childhood by one or more methods which include external orthotic bracing, spinal fusion surgery, and electrical stimulation (internal and/or external) of the paraspinal muscles.

Presently, the most widely used clinical method employed to diagnose, assess, and track the course of the disease is standard X-ray imaging. Since there are no reliable methods yet available to predict the rate of progression of the disease, the patient is examined on a regular basis. Typically, a child will be subjected to a large number of X-rays over the course of the disease regardless of the treatment modality implemented. In many cases, no treatment is warranted, but the child is X-rayed periodically to verify that the curve has not progressed significantly. It therefore becomes highly desirable to develop a technique of detecting and monitoring scoliosis which will minimize or eliminate X-ray exposure. In recent years, great emphasis has been placed on the need to develop effective, safe methods of screening children in public schools.

Aside from the issue of safety, the X-ray instrumentation currently used does not lend itself optimally to the rapid assessment of scoliosis. For example, just the right contrast must be obtained and then the equipment must be run by a radiological specialist. Further, the orthopedic surgeon must ponder the X-ray and then perform certain geometric operations on the image in order to extract quantitative information regarding the nature of the spinal curvature. Another parameter which is becoming increasingly important to measure is the amount of vertebral rotation which accompanies the lateral curvature of the spine. This is presently difficult to accurately assess using X-ray.

Not many alternative means to X-ray for assessing scoliosis appear in the literature. One method currently under limited evaluation is called the Moire technique. This is an optical photographic technique which detects bilateral nonsymmetry in the surface features of the back. The method employs the principle of interference fringes. The patient's back is photographed through an interference screen or defraction grating. This results in a set of contour-line shadows on the photograph which is indicative of the surface topology of the back. The main shortcomings of this system are two-fold. First, there are no established scientific correlative studies relating visual surface features to spinal curvature. Secondly, the device is primarily aimed at screening rather than the quantitative assessment of the magnitude of the spinal curvature. Thus a system and method with which spinal curvature could be directly measured which can be repeatedly used without damage to a child or other person would be highly desirable.

The present invention employs an ultrasound imaging system for scanning the back. A wide variety of ultrasound imaging systems for medical purposes have been developed although none of them known to me appear to be appropriate for scanning the back. U.S. Pat. Nos. 4,271,842 and 4,272,991 disclose typical ultrasound scanners in the prior art.

SUMMARY OF THE INVENTION

It is an object of the invention to provide apparatus for imaging of skeletal structure that overcomes the disadvantages of the above prior art.

It is another object of the invention to provide an ultrasound scanning system including a means for scanning ultrasound transducers along the back while providing a signal representative of the transducers' position along the back.

It is a further object of the invention to provide an ultrasound system which is particularly well-suited for imaging of the spinal column and the rib structure adjacent the spinal column.

It is an additional object of the invention to provide an ultrasound imaging system which provides one or more of the above objects in a system that can provide a diagnostic image in a single scan.

It is a further object of the invention to provide an ultrasound imaging system that provides one or more of the above objects in a system that provides data quickly so that it is utilizable in real time by the physician.

It is another object of the invention to provide a skeletal imaging system that is safe and economical so that it can be utilized in regular periodic treatment of children and other persons.

It is again a further object of the invention to provide an ultrasound imaging system that provides skeletal representations that are accurate and are easily correlated with established scientific norms.

The invention provides an ultrasound imaging system for scanning the human back. There is at least one ultrasound transducer for generating an ultrasound signal, for receiving an ultrasound signal, and for producing an electrical signal representative of the received ultrasound signal and a means for supporting the transducer and moving it along the human back. There is a means responsive to the electrical signal for producing a range signal representative of the distance from the transducer of objects interacting with the ultrasound signal, and a means for producing a position signal representative of the transducer position along the back. There is a means responsive to the range signal, and the position signal for producing an output signal representative of the structure of the body.

Preferably, the means for producing a position signal includes a means for referencing the position of the means for supporting the transducer to at least one reference point on the back and a means for producing a position signal representative of the position of the transducer in the means for supporting.

Preferably there is a plurality of transducers and the means for supporting and moving the transducers comprises a means for moving the transducers along lines parallel to the line connecting the spinal cervix and sacrum of the patient.

Numerous other features, objects and advantages of the invention which will become apparent from the following detailed description when read in conjunction with the accompanying drawings.

BRIEF DESCRIPTION OF THE DRAWING

In the drawing

FIG. 1 shows an imaging system according to the invention with the transducer transport portion of the system in position to image a portion of a patient's ribs and spinal column;

FIG. 3 shows a front view of the transport system of FIG. 2;

FIG. 4 shows a cross-sectional view of the transport system taken through line 4—4 of FIG. 3;

FIG. 6a shows a side view of an alternative embodiment of a portion of a transducer transport system according to the invention;

FIG. 6b shows a top view of the portion of the transport system of FIG. 6a;

FIG. 8d shows the arrangement of FIGS. 8d.1 and 8d.2 which in turn show the electronic circuitry for the non-linear time-gain amplifier, including the echo discriminator (rf detector and comparator), utilized in FIG. 7;

FIG. 8g (located after FIG. 6) shows the arrangement of FIGS. 8g.1 and 8g.2 which, in turn, show the electronic circuitry for the high-speed A/D converter and memory buffer system utilized in the embodiment of FIG. 7;

FIG. 8h (located after FIG. 8g on the same sheet of drawings as FIG. 6) shows the arrangement of FIGS. 8h.1 and 8h.2 which, in turn, show the electronic circuitry for the control logic for data expansion which is part of the high-speed A/D converter and memory buffer system utilized in the embodiment of FIG. 7;

DESCRIPTION OF THE PREFERRED EMBODIMENT

Figure 2:
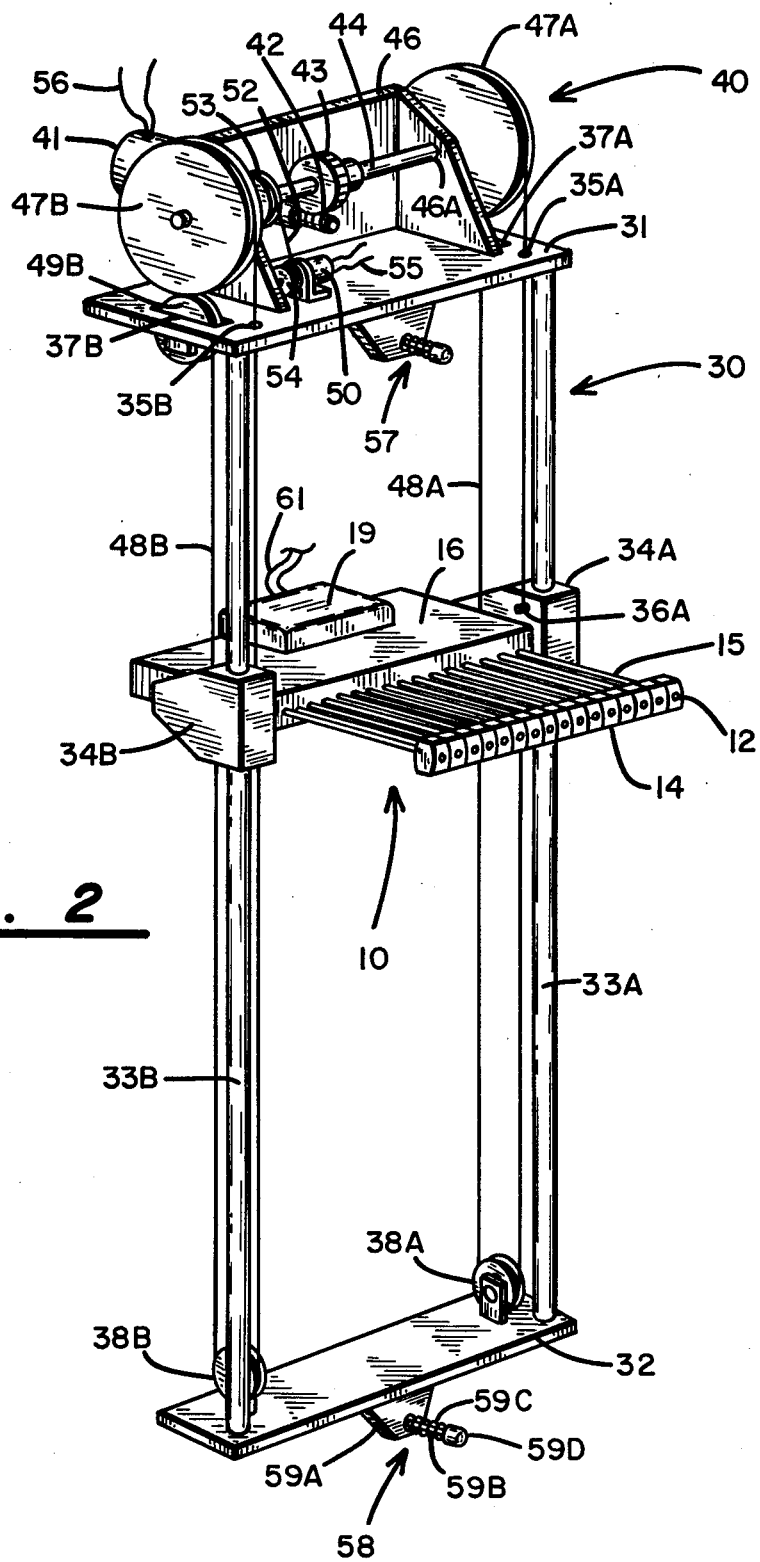
FIG. 2 shows a perspective view of the transducer transport system of FIG. 1.

An exemplary embodiment of the preferred ultrasound imaging system, according to the invention, for scanning of the human back is shown in FIG. 1. The system includes several major subsystems, including a scanner head 10, a transport system 30 for orienting and moving the scanner head in a particular fashion, a microprocessor-based control and display console 60, and keyboard terminal 80. The scanner head 10 provides a means for acoustically coupling low-intensity ultrasound energy to the back of the patient 11. The transport system 30 moves scanner head 10 in a straight line between two anatomical landmarks—cervical reference means 31 and sacral reference means 32. Control for the scanning process, data processing, record storage, and output of results is provided by microprocessor-based system counsole unit 60 which iC which, in turn, communicates with a Shugart SA-400 mini-floppy drive 75D, available from Harold E. Shugart Company, Inc., 1415 Gardena Avenue, Glendale, CA 91204. The display system includes three Matrox MSBC-512 graphic display boards, such as 84A, a Matrox MSBC-2480 alpha display board, 84B, an Axiom EX-850 printer 84C, and a Ball TV-120 display 84D. The Matrox display boards can be provides a means of inputing scanner control commands as well as pertinent patient information.

In order to clearly illustrate the invention, the description will contain three parts. First, a brief description of the mechanics of ultrasound will be presented. Second, a detailed description of the structure and electronic circuitry of the preferred embodiment will be given. Finally, a description of the operation of the invention including the principle features of the invention will be given.

ULTRASOUND MECHANICS

If a mechanical sound wave in an ultrasonic frequency range (typically 1 MHz to 10 MHz) is generated and acoustically coupled to biological tissue, the wave will propagate through the tissue at a velocity determined by the physical properties of the tissue. Reflections or "echoes" will occur whenever the velocity of propagation of the sound wave is altered. Interfaces between different tissue types within the overall biological media, in general, present a change in propagation velocity and hence a portion of the incident energy is reflected. The magnitude of an echo is proportional to the magnitude of the incident energy and the change in velocity at the interface. For example, when ultrasonic energy traveling at 1580 m/s through a layer of muscle tissue encounters bone, the velocity of propagation is increased to 4800 m/s and about 40% of the energy incident on the bone will be reflected in the form of an echo.

Figure 5A:
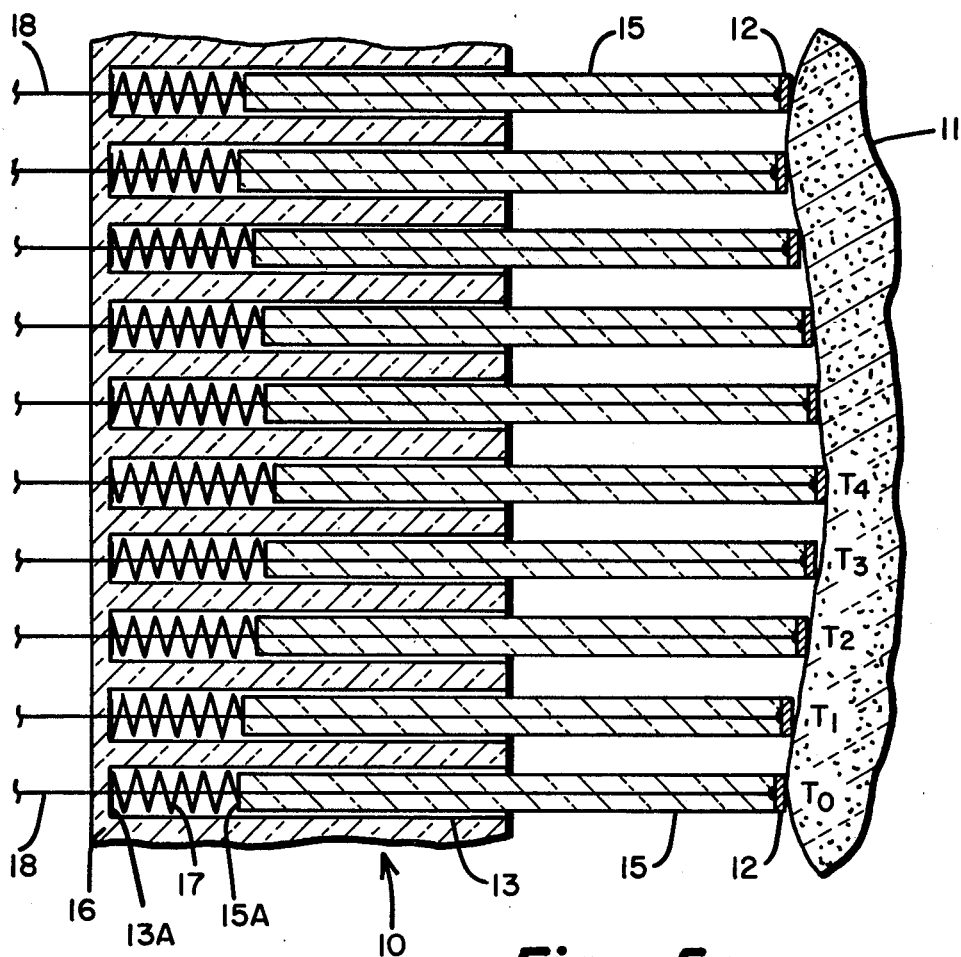
FIG. 5a shows a cross section of the scanner head taken through line 5a—5a of FIG. 3 and showing the transducers pressed against a section of the patient's back.

Low power (typically less than 100 mW/cm$^2$ average) ultrasound may be easily generated by the application of a short pulse of voltage (200 V for 1 $\mu$s typical) to an appropriately constructed piezoelectrical crystal such as 12 (FIG. 5a). Momentary deformation of the crystal 12 ensues and it vibrates for a short period of time at its natural resonant frequency (2.25 MHz for the present embodiment). Consequently, a low intensity mechanical pressure wave or sound wave is set up in the media 11 to which the element is coupled.

Conversely, the presence of an incoming ultrasonic wave front in the form of an echo may be detected because the resulting pressure on the crystal 12 produces a voltage across the crystal 12. Such crystals 12 are called ultrasound transducers and the same transducer is typically employed to both transmit and receive pulses of ultrasonic energy.

By aiming the transducer 12 at a target in a particular direction within a defined coordinate system and measuring the time elapsed between the transmission of a sound wave and the reception of an echo from the target it is possible to calculate the distance or range to the target, and subsequently to locate the position of the target within the coordinate system. Further, it is possible to determine certain features of the target (for example surface texture) by analyzing the resulting echo waveform.

In the prior art, medical ultrasound has been employed to examine internal soft tissue organ structures. Frequently, a "target" structure is treated as a composite of many individual target components. The present disclosure will disclose how the above principles of ultrasound may be applied under the management of a microprocessing system to perform a specific type of scan of the human back.

STRUCTURAL AND ELECTRICAL DESCRIPTION

We now proceed to the detailed structural description of the apparatus according to the invention. A perspective view of the scanner 10 and the transport system 30 for moving the scanner head 10 is shown in FIG. 2. A frontal view of the same system is shown in FIG. 3 and a cross section taken through lines 4—4 of FIG. 3 is shown in FIG. 4. FIG. 5a shows a cross section of the scanner head taken through lines 5A—5A of FIG. 3. The transducer shoes 14 of FIG. 3 are omitted in FIG. 5a for clarity. All these figures will be discussed together.

Together the scanner head 10 and the transport system 30 provide a means for supporting and moving the transducer 12 along the back. In the embodiment shown there are sixteen transducers such as 12. Each transducer, such as 12, is embedded in a transducer shoe, such as 14, which is attached to the end of a movable plunger, such as 15. The scanner head 10 comprises scanner body 16 having sixteen cylindrical bores, such as 13. Each of the bores 13 is of a diameter just slightly larger than the plungers such as 15, and each of the plungers 15 slide within one of the bores such as 13. Within each of the bores, such as 13, there is a spring such as 17, one end of which seats against the bottom 13A of its respective bore 13 and the other end of which seats against the end 15B of plunger 15 opposite transducer 12. A wire, such as 18, is electrically connected to each of the transducers, such as 12, and extends through the plunger 15 and bore 13 through scanner body 16 into scanner electrical box 19 where they are connected into the transducer electronics (see below) and ultimately to flexible electrical cable 61.

Scanner transport system 30 includes a frame top plate 31 and a frame base plate 32 separated and connected by a pair of scanner head rails 33A and 33B. Rails 33A and 33B pass through a cylindrical bore within scanner head blocks 34A and 34B respectively. The bore of blocks 34A and 34B is just slightly larger than the diameter of rails 33A and 33B respectively so that blocks 34A and 34B slide easily on their respective rails. Scanner body 16 is secured to the inner side of blocks 34A and 34B so that the whole scanner head 10 moves as a unit on rails 33A and 33B. The major portions of the drive system 40 for the scanner head 10 is mounted on top plate 31. Drive means 40 includes motor 41 which drives a worm and wheel gear (42 and 43 respectively). Wheel 43 is supported by and locked to axle 44 which is, in turn, supported on frame 46 and turns in bushings 46A and 46B (not shown) in frame 46. Frame 46 is mounted on plate 31 to support the drive system. Groved drums 47A and 47B are connected to either end of axle 44 and turn with the axle 44. A pair of cables 48A and 48B seat in the grooves of drums 47A and 47B respectively, pass through holes 35A and 35B respectively in top plate 31 and are fastened to pins 36A and 36B set in blocks 34A and 34B respectively. The other end of cables 48A and 48B pass over guide pulleys 49A and 49B mounted in slots 37A and 37B in plate 31, then pass under pulleys 38A and 38B mounted on the base plate 32 and return upward to fasten to pins 39A and 39B secured to blocks 34A and 34B respectively.

FIGS. 6a and 6b show an alternative embodiment of the transport system which may be used if it is desired that the transducer remains tangent to the curvature of the surface of the back. We have found experimentally that this is often advantageous in maximizing the reflected energy received and thus maximizing the signal strength from the transducers. In FIGS. 6a and 6b the motor and other elements for moving the head are not shown for clarity and as these aspects would be similar to those shown in FIGS. 1 through 4. This embodiment includes a scanner head 9 having a rotational degree of freedom which permits the transducer element 149 to be tangent to the surface of back 11. Scanner head 9 includes blocks 144A and 144B which slide on rails 140A and 140B as described above. Probes 141A and 141B are attached to brackets on the lower and upper ends of rails 140A and 140B also as described earlier. Blocks 144A and 144B are connected to scanner body brackets 144C and 144D respectively by pivot pins 145A and 145B respectively. Scanner body brackets 144C and 144D are C-shaped brackets which fit about the sides of scanner body 142C holding it securely in both the vertical direction and the direction into the plane of the drawing (FIG. 6a), but permitting it to slide in the horizontal direction of the drawing. Y-brackets 142A and 142B are secured (by screws not shown) to scanner body 142C. Rollers 146A and 146B are attached to the ends of the "Y" of brackets 142A and 142B by axles 146C and 146D respectively. Axles 146C and 146D fit within a bore of rollers 146A and 146B so that the rollers may rotate freely on the axles. Plungers 147A and 147B slide within bores in scanner body brackets 144C and 144D respectively and seat between Y-brackets 142A and 142B and springs 147D and 147C respectively within the bores. Transducer plungers such as 143 are spring-loaded (springs not shown), ride in bores in scanner body 142C, and have transducer shoes, such as 148 holding transducer elements, such as 149, mounted on the distal ends of the plungers as in the embodiments described with reference to FIGS. 2 through 5.

The apparatus described in the preceding three paragraphs comprises a means for moving the transducers over a field so as to define a plane. The field is the whole 3-dimensional space moved through by the transducers 12, 149 as they traverse the back while the plane may be any generalized plane defined by the movement of the transducers such as 12 or 149. The plane is generalized in the sense that it may or may not be a flat plane; that is, it may either be the actual "plane" through which the transducer elements 12 or 149 move, or it may be a plane which is abstracted from the space through which they move. For example, in the embodiment of FIGS. 6a and 6b and using the linear position transducers of FIG. 5b, the plane may be a curved surface such as the plane of the back, or if may be a flat plane essentially parallel to the plane in which rails 33A and 33B lie. The invention relates to a means for storing data in an array such that the position of the data in an array corresponds to the position of the transducer such as 12 or 149 in this generalized plane when the data is produced.

Position transducer 50 is mounted on top plate 31 and is driven by transducer drive belt 52 which rotates about position transducer drive pulley 53 which is secured to axle 44 and pulley 54 which is fastened to the drive shaft of position transducer 50. The position transducer 50 is a potentiometer connected nominally across 0 to 12 volts d.c. (typical operating range 2-8 volts d.c.). As pulley 59 turns, a wiper within the potentiometer 50 moves and produces a voltage proportional to the distance which the scanner head 10 has moved. Wires 55 which carry the output signal of position transducer 50 and wires 56 which carry the input current to motor 41 form flexible electrical cable 62 (FIG. 1).

Located on the transducer support system 30 are means 57 for referencing the ultrasonic transducer position to a cervical reference point and a means 58 for referencing the ultrasonic transducer position to a sacral reference point. Each of these reference means includes a bracket such as 59A which supports a push rod, such as 59B which is mounted in a hole through bracket 59A. A spring 59C seats between one side of bracket 59A and a cap 59D mounted on the end of push rod 59C. Together the reference means such as 57, scanner head 10, the cables such as 48A, drums 47A, axle 44, drive pulley 53, drivebelt 52 and position transducer 50 provide a means for producing a position signal representative of the position of transducer 12 along the back.

Figure 5B:
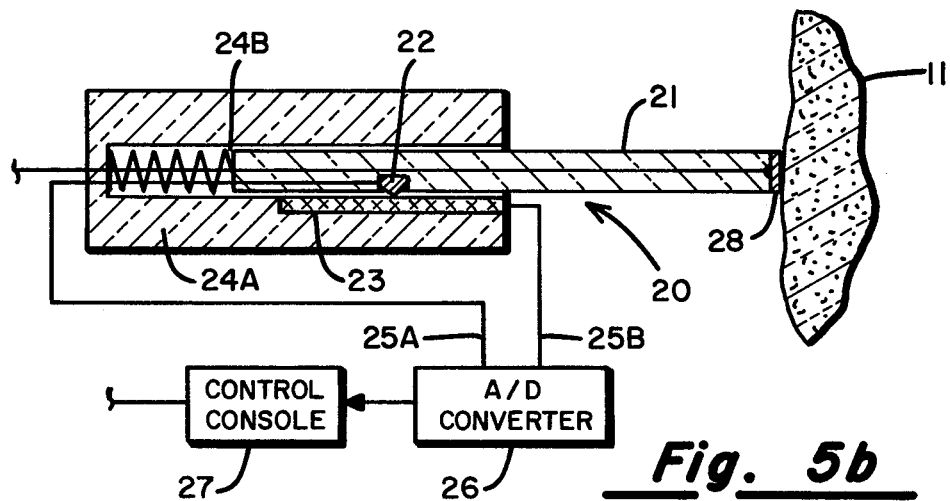
FIG. 5b is a cross-sectional side view of an alternative embodiment of the scanner head showing a linear position transducer.
Figure 8B:
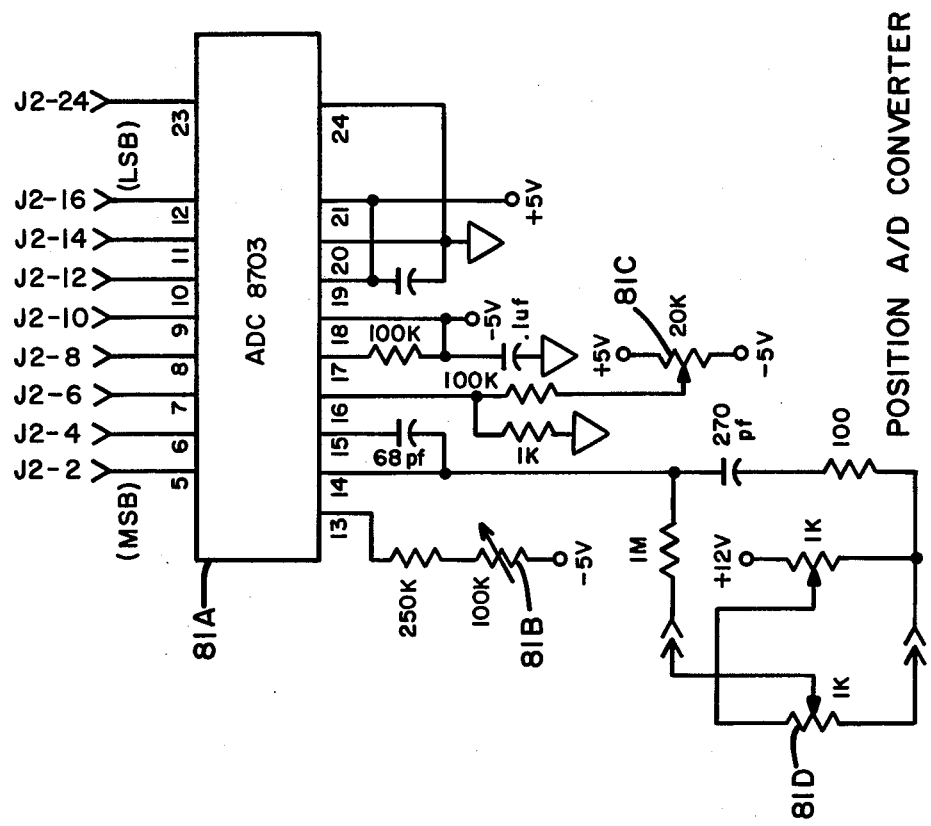
FIG. 8b shows the electronic circuit of the A/D converter for scanner head position utilized in the embodiment of FIG. 7.

FIG. 5b is a cross-sectional side view of an alternative embodiment of the scanner head. In the figure the transducer sleeve is again not shown. This embodiment includes a linear position transducer 20 which produces a signal proportional to the position of plunger 21. Linear position transducer 20 includes a contact 22 secured on the bottom side of plunger 21 and extending a small distance beyond the side of the plunger 21, and a resistance element 23 embedded in scanner body 24A with its surface exposed along a section of bore 24B so that contact 22 moves along resistance element 22 as plunger 21 moves in bore 24B. Wire 25A is attached to contact 22 and wire 25B is attached to one end of resistance element 23 and both wires 25A and 25B are input to an A/D converter 26 to complete a circuit through resistance element 23. The voltage through the linear transducer circuit 20 is proportional to the position of contact 22 on resistance element 23 and thus is a measure of the position of plunger 21 and ultimately of the position of transducer 28. The A/D converter translates the voltage to a digital signal in a manner similar to that described below with reference to FIG. 8b. The digital signal is input to the central console 27 for use as will be discussed below.

Note that wires 18 (in FIG. 5a) and 24A (in FIG. 5b) are shown straight only for clarity. In actuality they are coiled in the bore so that they may extend and contract as plungers 15 and 21 move.

Figure 7:
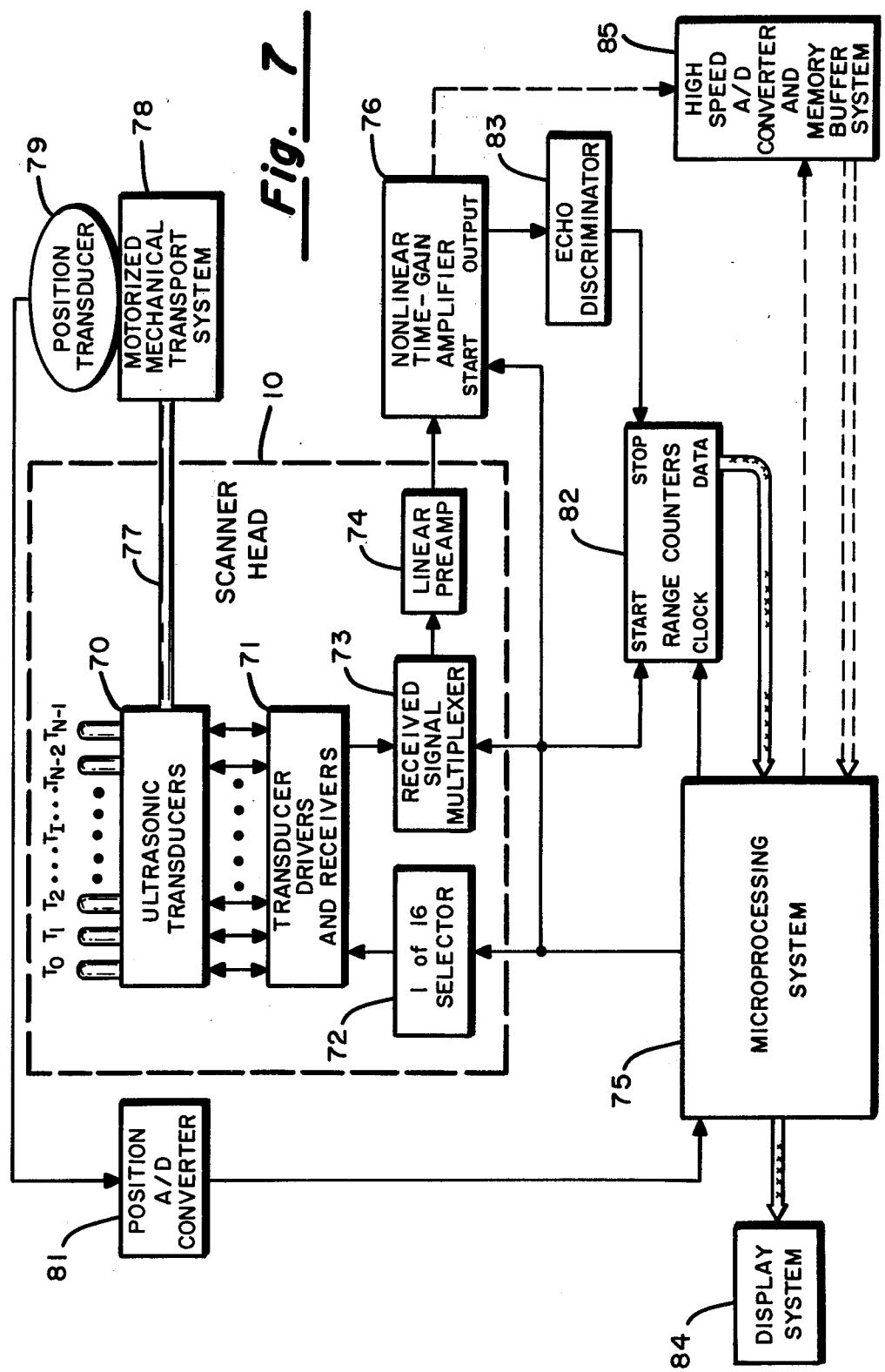
FIG. 7 shows a block diagram of the preferred embodiment of the ultrasound imaging system according to the invention.

FIG. 7 shows a block diagram of the electronic system utilized in the embodiment of the invention shown in FIG. 1. The electronics included in scanner head 10 is enclosed in the dashed rectangle. In this diagram the transducers are indicated as $T_0, T_1, T_2 \ldots T_I \ldots T_{N-2}, T_{N-1}$ for purposes of the generalized discussion below. In the preferred embodiment there are sixteen such transducers and thus, N is equal to 16. The transducer driver and receiver circuitry 71 delivers signals to and receives signals from the ultrasonic transducers 70. One of sixteen selector circuitry 72 receives signals from the microprocessor system 75 and in turn, applies signals to the transducer drivers and receiver circuitry 71. Received signal multiplexer 73 receives the signals derived from the reflected ultrasonic waves from the transducer driver and receiver circuitry 71. A signal from the microprocessor system 75 is applied to received signal multiplexer 73 to inform it which signal should be recognized. The signals recognized by the received signal multiplexer 73 are passed to the linear preamp 74 and, after amplification, proceed on to the nonlinear time-gain amplifier 76. The doubleline 77 indicates a mechanical linkage between the motorized mechanical transport system 78 and the ultrasonic transducers 70. As discussed above, there is also a mechanical linkage between motorized mechanical transport system 78 and position transducer 79. The signal from position transducer 79 is applied to position A/D converter 81 and the digital output from the position A/D converter is applied to the microprocessor system 75. The microprocessor system 75 applies a clock signal and a start signal to range counters 82. The output of the nonlinear time gain amplifier 76 is applied to echo discriminator 83 and when an echo is detected a signal is applied to the stop input 83C of range counters 82. The signal from the range counters is applied to the microprocessor system 75. In this embodiment the microprocessor 75, the range counters 82, and the echo discriminator 83 together comprise a means for providing a range signal representative of the distance of objects interacting with the ultrasound signal. The microprocessor system 75 provides an output to the display system 84. High-speed A/D converter and memory buffer system 85 is an optional part of the system which will be discussed below. This system 85 receives signals from nonlinear time-gain amplifier 76 and microprocessor system 75;

these signals are indicated by dotted lines to indicate they are optional. The signal from high-speed A/D converter and memory buffer system 85 is applied to microprocessor system 75.

FIGS. 8a through 8h show details of the circuitry of each of the portions of the circuitry shown in FIG. 7. With the exception of the time-gain amplifiers, the particular elements of the subcircuits are for the most part conventional and those skilled in the art will be able to develop such circuits and alternatives to such circuits from the description given and standard electronic literature. However, the various parts used and sources for those parts will be presented in order to fully elucidate the construction of the invention.

Figure 8A:
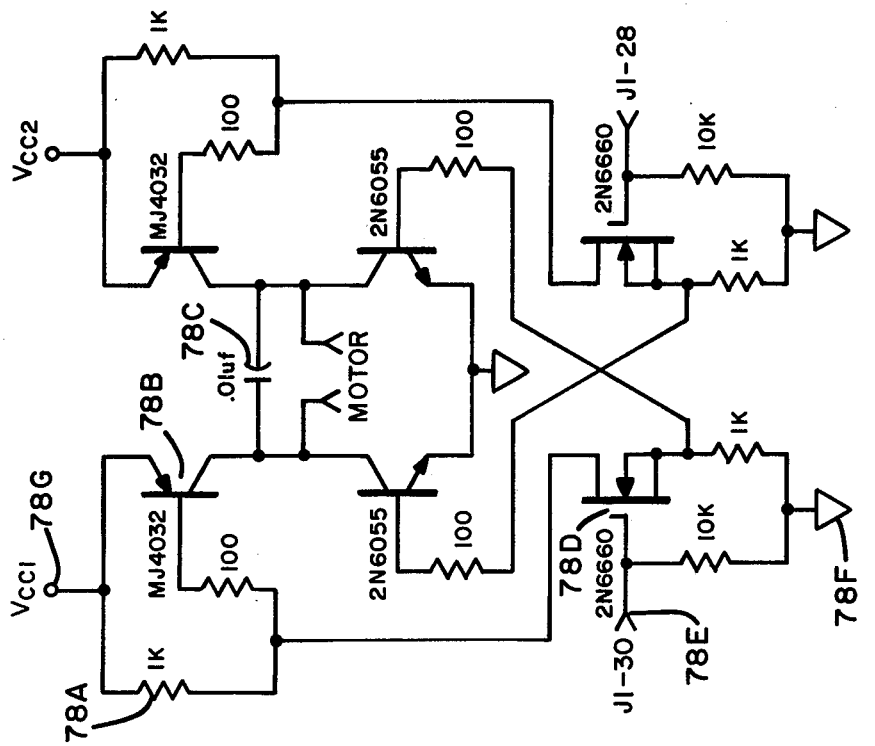
FIG. 8a shows the motor control circuit utilized in the embodiment of FIG. 7.
Figure 8C:
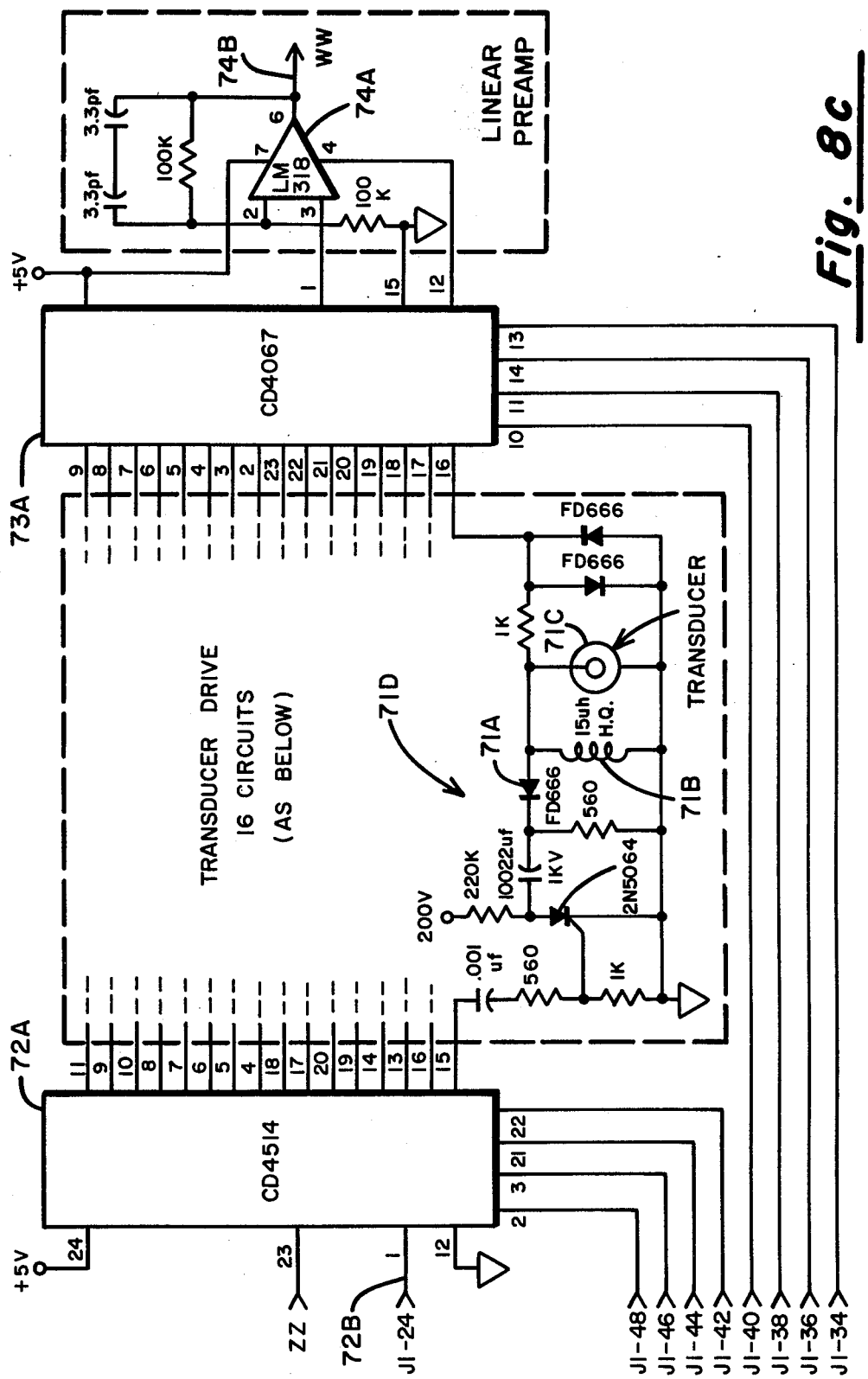
FIG. 8c shows the electronic circuitry for the transducer drivers and receivers including the 1 of 16 selector, the received signal multiplexer and the linear preamp utilized in the embodiment of FIG. 7.

The motor control circuitry is shown in FIG. 8a. In this figure, and the subsequent figures showing electronic circuitry, standard electronic symbols for the various circuit elements are used. Each of these elements will be pointed out in the first figure in which they are encountered. In FIG. 8a, a resistor is shown at 78A, with the value of the resistor given in ohms alongside the resistor. A transistor is shown at 78B, with the standard trade designation for the transistor type given alongside the transistor (MJ4032 for transistor 78B). A capacitor is shown at 78C with the value of the capacitance, 0.01 $\mu f$, given next to the capacitor. A field effect transistor (FET) is shown at 78D, with the standard trade designation of the FET type, 2N6660 given next to the FET. The symbol at 78E, shaped like the tail of an arrow, indicates a connector. The number next to the connector symbol, such as J1-30 at 78E, indicates where the connection is to be made. For example, the J1-24 at 72B in FIG. 8c is connected to the J1-24 connection at 76A in FIG. 8d. Furthermore, all such symbols which begin with a J1, J2, or J3 designation refer to standard connection points on an ISBC 80/30 single board computer (microprocessor system) made by the Intel Corporation, 3065 Bowers Avenue, Santa Clara, CA 95051. Triangles, such as 78F, indicate a digital signal ground, while small circles, such as at 78G indicate a plus or minus voltage connection. The voltage is given next to the circle, either as a plus or minus numerical voltage or as $Vcc_1$ or $Vcc_2$ which indicate positive DC power supply voltages. Normally $Vcc_1$ would be set at +12VDC and $Vcc_2$ would be set at +5VDC. The higher voltage ($Vcc_1$) runs the motor while the scanner head is being raised or returned to the ready position while the lower voltage $Vcc_2$ is switched to when the scan is being conducted. This saves time during the return of the scanner head. The circuitry for the position A/D converter for the scanner head position is given in FIG. 7b. The large rectangle 81A is an analog-to-digital converter chip such as that made by Analog Devices, Inc., Route 1, Industrial Park, P.O. Box 280, Norwood, MA 02062. The designation for this chip and other chips used in the electronics is shown in the rectangle. At 81B a variable resistance is shown, with the maximum value of the resistance (100 Kohms) given next to the symbol. The symbol at 81C indicates a potentiometer with the maximum value of the resistance of the potentiometer (20 Kohms) given next to the symbol for the potentiometer. The 1 Kohm potentiometer at 81D is the potentiometer within the position transducer 50 in FIG. 2.

The electronic circuitry for the one of sixteen selector, the transducer drivers and receivers, the received signal multiplexer and the linear preamp are shown in FIG. 8c. The one of sixteen selector circuitry is essentially contained in integrated circuit chip 72A. This is a standard integrated circuit chip which may be purchased, for example, from RCA Solid State, Box 3200, Summerville, NJ 08876. Symbol 71A represents a signal diode, with the standard trade designation for the diode given next to the symbol. 71B is an inductance with the value for the inductance given next to the symbol. Transducer 71C is a 2.25 MHz transducer produced by Harrisonics of Stamford, CT, 06902. Received signal multiplexer is also essentially contained in an integrated circuit chip 73A with the standard trade designation number given on the chip. Symbol 74A in the linear preamp circuit represents an operational amplifier, such as that produced by National Semiconductor Corporation, 2900 Semiconductor Drive, Santa Clara, CA 95051. The transducer drive and receiver circuitry shown at 71D is reproduced sixteen times, once for each transducer in the preferred embodiment and each of the sixteen circuits are connected between selector 72A and multiplexer 73A as indicated by he dotted lines in the drawing. The WW designation given at point 74B indicates a wire connection to the terminal labeled WW at 76C in FIG. 8d.1. Likewise, other points with double lettered designations elsewhere in the drawings indicate wire connections between identically labeled points.

The nonlinear time-gain amplifier and echo discriminator is shown in FIGS. 8d.1 and 8d.2. The two figures should be placed side-by-side as shown in FIG. 8d and are connected along line 76A. In FIG. 8d.1 the only new symbol introduced is shown at 76B. This is a dual gate FET, and the standard trade designation for the FET is given just above the symbol. The echo descriminator circuitry is shown in FIG. 8d.2. This includes an RF detector and a comparator as shown. The three transistors and diode indicated by 83A are formed in a single standard chip with the trade designation CA3146. All other elements in the circuits have been previously described.

Figure 8E:
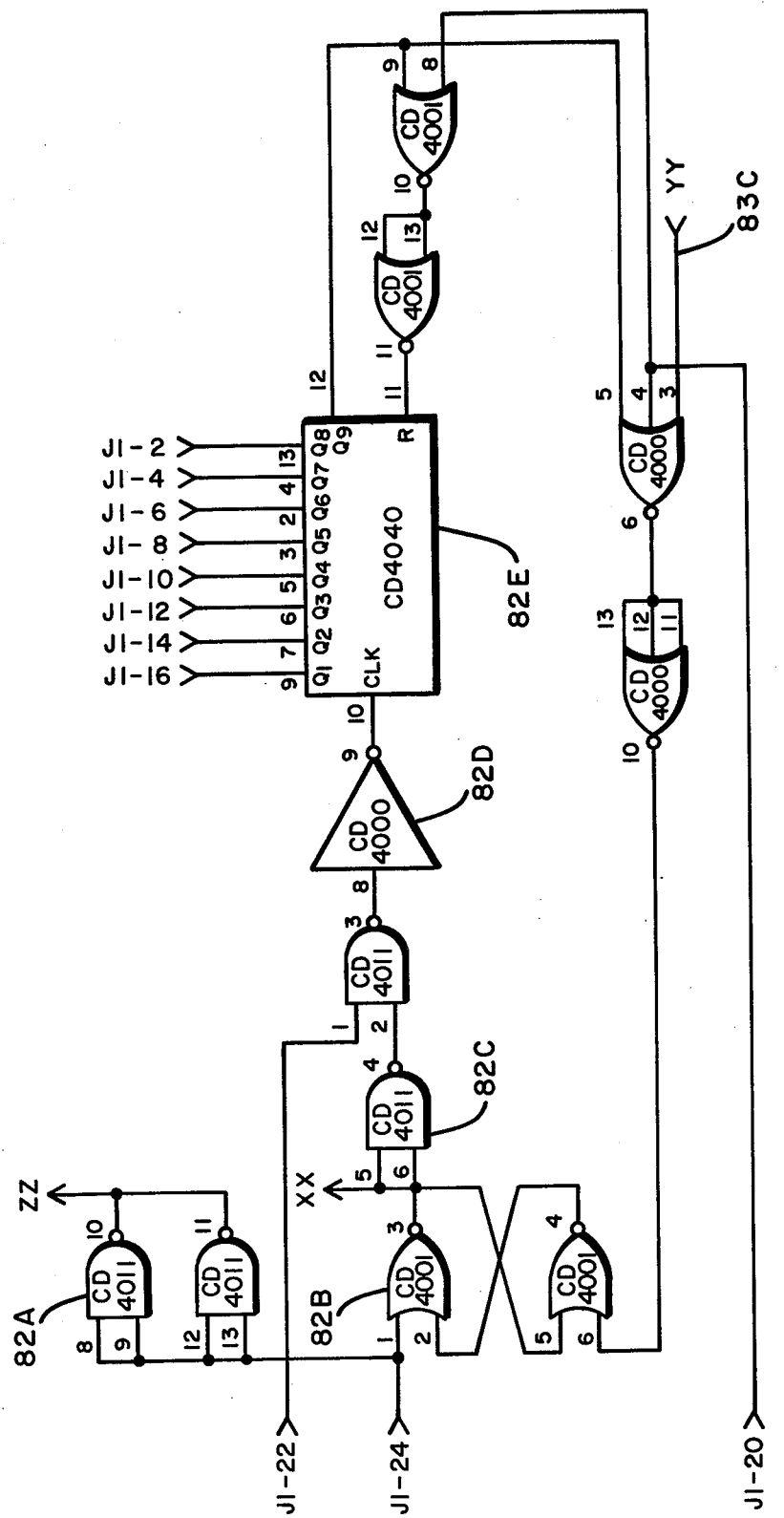
FIG. 8e shows the electronic circuitry for a range counter utilized in the embodiment of FIG. 7.

The first of two range counters is shown in FIG. 8e. This circuit includes four NAND gates, such as 82A, six NOR gates, such as 82B, and an inverter shown at 82D. The four gates designated CD4011 are contained in a single integrated circuit package, as are the four gates indicated by the designation CD4001 and the two gates and inverter indicated by the designation 4000. 82E is a binary counter, with the standard trade designation indicated on the drawing.

Figure 8F:
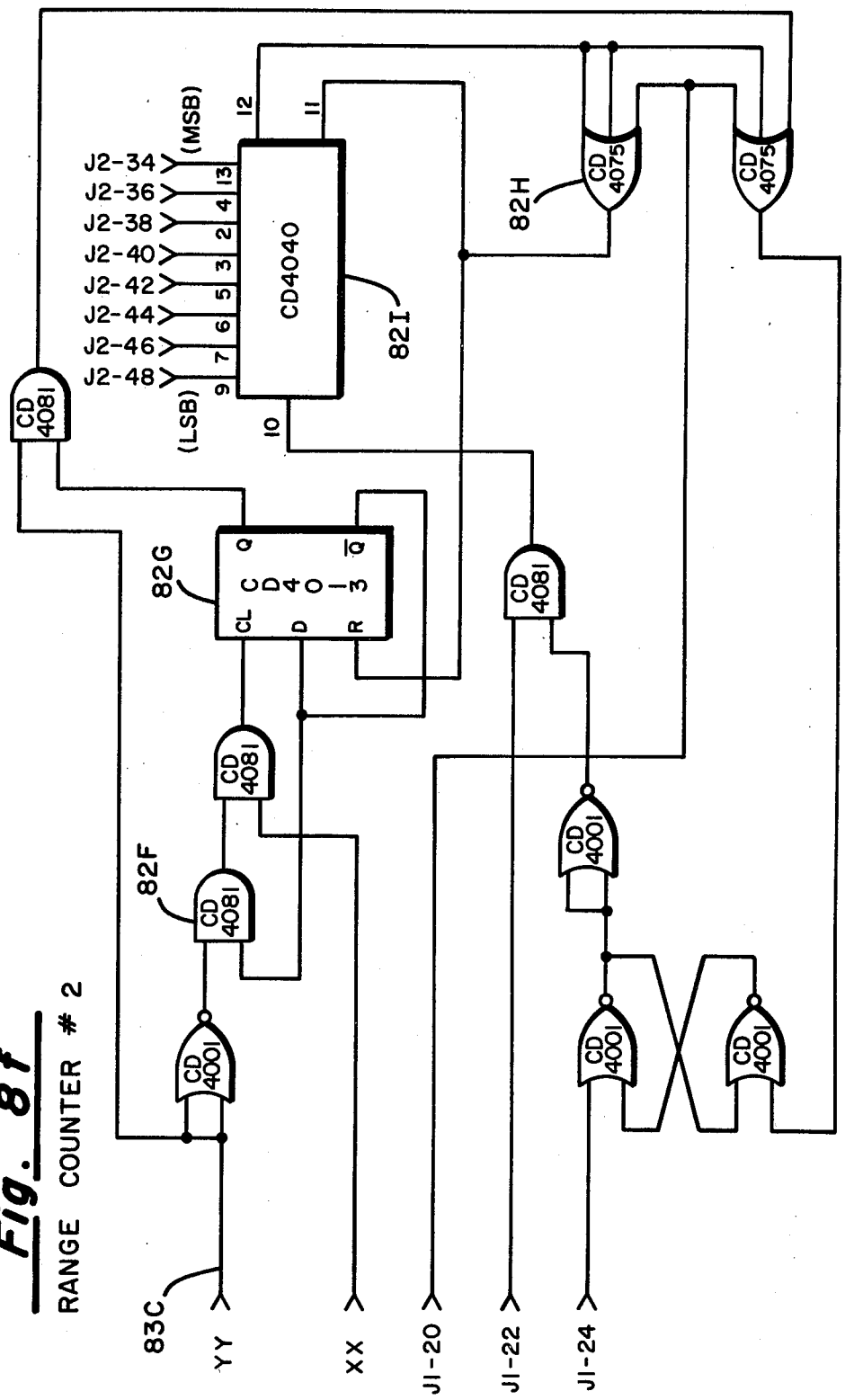
FIG. 8f shows the electronic circuitry for a second range counter utilized in the embodiment of FIG. 7.

The circuitry for a second range counter is given in FIG. 8f. This circuitry includes four AND gates 82F. Element 82G is a flip-flop, with the standard designation for the flip-flop on the drawing. The OR gates, such as 82H are located on a single standard chip.

The circuitry for the optional high-speed A/D converter and memory buffer system is shown in FIGS. 8g.1 and 8g.2. These figures should be arranged as shown in FIG. 8g (located on the same sheet drawing as FIG. 6) and when this is done, the connections between the two parts of the circuitry along line 85A is clear. Symbol 85R indicates an analog signal ground. Digital signal grounds and analog signal grounds are maintained separately in the system. The principal parts of this system include the A/D converter 85B, model TDC1007PCB manufactured by TRW, Inc., 10880 Wilshire Blvd., Los Angeles, CA 90024 and the model TC106 high-speed shift registers, such as 85C, also manufactured by TRW, Inc. Symbol 85D represents a standard type BNC connector. In FIG. 8g.2, 85E is a high-speed D/A converter built by TRW (model TDC1016), and 85F is an operational amplifier with the standard designation LM10 such as may be purchased from National Semiconductor Corporation at the address given above. The control logic for utilizing the high-speed A/D converter and memory buffer system in the data expansion process (which will be discussed below) is shown in FIGS. 8h.1 and 8h.2. These two drawings should be arranged as shown in FIG. 8h (located on the same sheet drawing as FIG. 5a), and when this is done the electrical connections between the two figures along line 85H is evident. In FIG. 8h.1 the triangles 85I are SN7407 drivers, such as those available from Signetics Corporation, 811 E. Arques, P.O. Box 9052, Sunnyvale, CA 94086. The arrow heads, such as 85J indicate connections to other points in the drawing with the same designation (for example, point 85J, connects to the CL5 connector 85G in FIG. 8g.2). The arrow head indicates the direction of signal flow. Rectangle 85k represents a 93L10 type synchronous four-bit decade counter, such as that available from National Semiconductor Corporation at the address given above. 85L is a 10 MHz crystal available from International Crystal Mfg. Co., Inc., 10G North Lee St., Oklahoma City, OK, 73102. Rectangle 85M is a type CD40103 counter and 85N is type CD4098 dual monostable multivibrator both of which are available from RCA Solid State. FIG. 8h.1 also contains a series of switches such as 85P, which are conventional single-pole, single-throw switches. The circuit of FIG. 8h.2 contains four type 8216 four-bit bidirectional bus drivers, such as 85Q, available from the Intel Corporation.

Figure 8I:
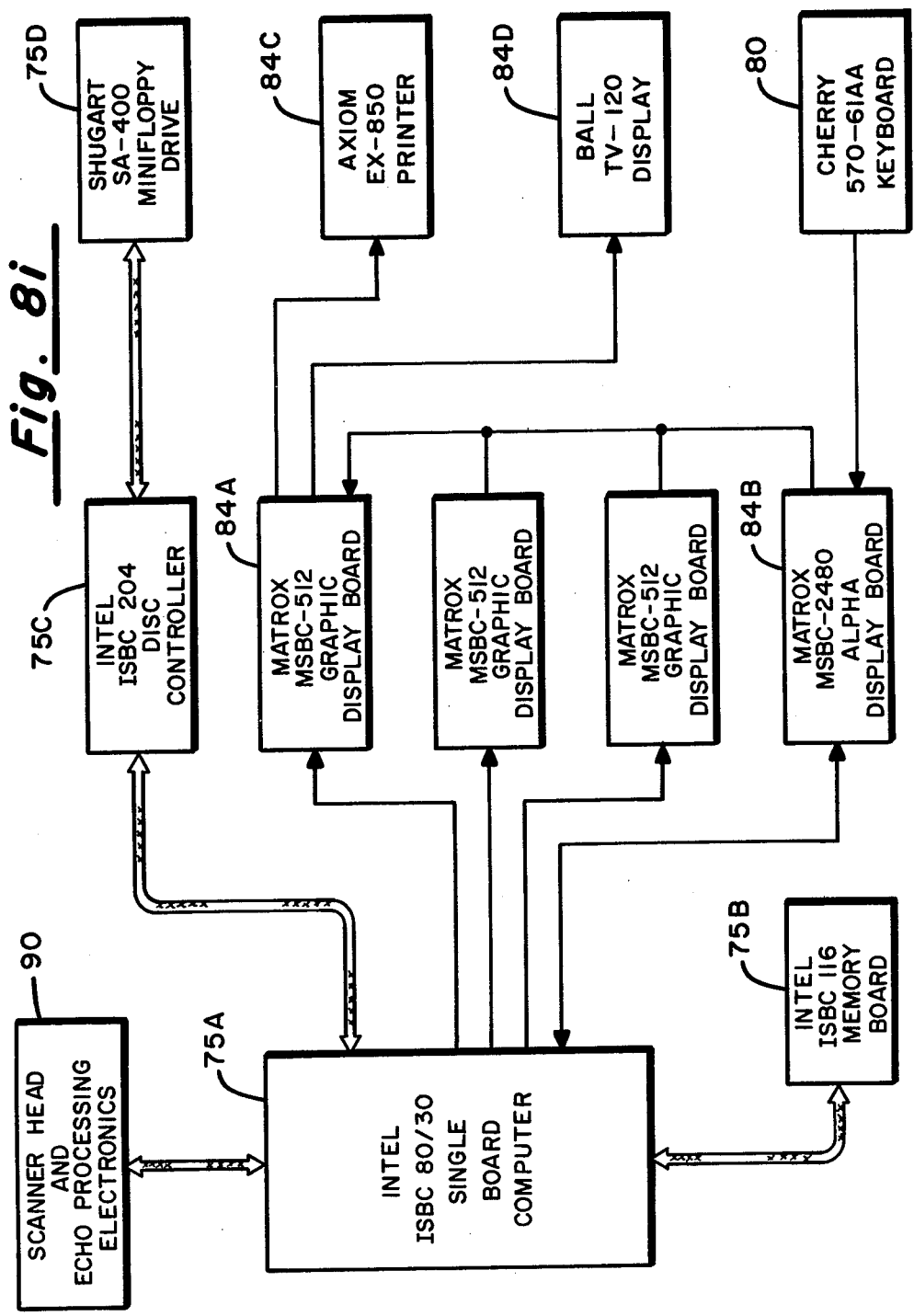
FIG. 8i shows the block diagram for the microprocessor system utilized in the embodiment of FIG. 7.

The block diagram of the microprocessor and display system is shown in FIG. 8i. The heart of the system is an Intel 8085 processor chip incorporated on an Intel ISBC 80/30 single board computer 75A, and an Intel ISBC 116 memory board 75B. This computer system is connected with the scanner head and echo processing electronics 90 as discussed above. For data storage, computer 75A communicates with Intel ISBC 204 disk controller 75C which, in turn, communicates with a Shugart SA-400 mini-floppy drive 75D, available from Harold E. Shugart Company, Inc., 1415 Gardena Avenue, Glendale, CA 91204. The display system includes three Matrox MSBC-512 graphic display boards, such as 84A, a Matrox MSBC-2480 alpha display board, 84B, an Axiom EX-850 printer 84C, and a Ball TV-120 display 84D. The Matrox display boards can be obtained from Matrox Ltd., 2795 Bates Rd., Montreal Quebec, Canada, the Axiom printer is available from Axiom Corporation, 5932 San Fernando Road, Glendale, CA 91202, and the Ball display is available from Ball Electronic Display division, P.O. Box 43376, St. Paul, MN, 55164. The display boards, such as 84A and 84B receive inputs from the computer 75A and communicate with each other (arrows). The Alpha display board 84B receives input from the keyboard 80 and applies a signal to computer 75A. Keyboard 80 is a Cherry 570-61AA keyboard available from Cherry Electrical Products, Corporation, 3625 Sunset Avenue, Waukegon, IL 60085. The system just described, including computer 75A, Memory 75B, controller 75C, display boards, such as 84A and 84B, minifloppy drive 75D, printer 84C, CRT display 65 and keyboard 80, when programmed with the software described below, comprise a means responsive to the range signal and the position signal and for producing an output representative of the structure of the body.

The materials out of which the invention is constructed are, for the most part, obvious from the functions performed, however, these will be briefly described for completeness. Rails 33A, 33B, 140A and 140B are preferably made of stainless steel, while plates 31 and 32 and frame 46 are made of aluminum, although any suitable metal or hard plastic material may be used. Wheels and pulleys, such as 47A, 49A, 38A, 53, 54, 146A and 146B may be made of a machineable plastic such as Teflon ®, although any other suitable plastic, metal or other material may be used. Likewise, blocks 34A, 34B, 144A, 144B, 144C and 144D and the transducer housings, such as 14 and 148 may made of Teflon ®, or similar plastics, fibers or metals. Rods, such as 15, 143 and 147A the scanner head bodies such as 16 and 142 and gears such as 43 and 42 may be made of brass or any other suitable metal or plastic material. Springs such as 17, 59C and 147C, as well as cables such as 48A may be made of stainless steel or any other suitable metal, compressed fiber, etc. Brackets 59A, 144C and 142B and rod 59B may be made of aluminum, Teflon ® or any similar metal or plastic while tip 59D may be made out of rubber, silicone rubber, or other plastics, fibers, etc. The transducer elements such as 12, may be made of barium titanate (referred to as K-85 ceramic by Harrisonics, Inc.). Resistance element 23 may be made of carbon or any other suitable resistor material.

FEATURES AND OPERATION

To perform a typical back scan a start command is entered via the console keyboard 80. The transport motor 41 elevates the scanner head 10 to the top of the transport rack 30. The transport rack 30 and scanner head 10 are then appropriately oriented on the back 11 of the patient (patient may be in the standing or prone position) with the cervical reference point 31 and the sacral reference point 32 contacting two well-known palpable anatomical landmarks of the spine such as C-7 (the seventh cervical vertebrae and the sacral crest or coccyx. The procedure of aligning the upper and lower reference points 31 and 32 of the transport rack 30 with the upper and lower landmarks of the spine also places the transducers 12 of the scanner head 10 in positive contact with the skin on the back 11 of the patient. The unique method of maintaining this contact for the duration of the scan is described in detail later in a section on the scanner head.

Following a momentary delay, the ultrasound transducers 12 in the scanner head 10 begin to sequentially emit pulses or bursts of ultrasound energy. Suppose that the "N" number of transducers in the array are numbered from left to right as $T_0, T_1, T_2 \ldots T_I \ldots T_{N-2}, T_{N-1}$ where I is the number of any arbitrary transducer in the array. $T_0$ first acting as an acoustic generator or transmitter emits a short pulse of sound or is said to be "fired." Immediately thereafter, $T_0$ is switched to a receiving mode. As the sound energy propagates through the tissues of the back, the interfaces of various tissue layers cause some sound energy to be reflected in the form of echoes. $T_0$, therefore, listens for a prescribed time period and detects any echo in this "window" of time. The echo signals are processed in a prescribed fashion by the scanner head electronic module 19 and by the system console 60 as described in detail later. $T_1$ then fires and begins listening, and so on, until $T_{N-1}$ has fired and listened. Following completion of this firing and listening sequence, the process is repeated for N transducers in periodic fashion.

Coincident with the transmitting and receiving activity of the transducers, the scanner head 10 moves mechanically away from the cervical reference point toward the sacral reference point. The "field" over which the transducer array scans has dimensions of "X" units wide by "Y" units in length. The computer software is configured such that a memory matrix is defined with "J" referring to rows and "I" to columns. The number of columns corresponds directly to the number of transducers (N) in a row across the scanner head 10. N will be set equal to 16 for purposes or example. The number of rows is equal to a selected number of equal subdivisions (J) in the length (Y) of the scan field. The number of rows will be selected as 480 for further illustration. The scan field may then be represented by a (J, I) matrix of 480×16 or 7680 discrete points. In general, a short burst of ultrasound energy is introduced at least once in methodical fashion at each one of these points in the field of scan and the resulting echo pattern or echo signature is analyzed at each point.

At each point in the field of scan, any echoes occuring are discriminated for selected features by an echo discriminator 83. Calculation of the range or distance between the transducer face and the relevant anatomical structure which produced a discriminated echo at a particular (Y, X) coordinate is performed. Each piece of range information is stored in the corresponding element in the (J, I) memory matrix. Range then becomes a third dimension and is directly related to "Z", the dimension of depth into the back at which the tissue interface producing the discriminated echo is located.

The ramification of this scanning process is that following the application of a one pass linear scan down the back there are potentially 7680 numbers contained in a memory map which may be subsequently rapidly processed to render information on the geometrical relationships between the various components of the dorsal skeletal system.

One important use of this information is to determine the presence or absence or abnormal lateral curvature of the spine (scoliosis) and, further, to automatically assess the severity or "degree" of such abnormal curvature. This is made possible by constraining the transducer array 70 to move in a well defined manner, namely a straight (when viewed from the back) line, between the cervical and sacral reference points. Each transducer element thus moves along the back along a line substantially (that is, within the variations of the back) parallel to the line between the reference points. The lateral curvature of the spine may then be referenced to a straight line drawn between these two points—two points through which the spine must pass regardless of its geometry between these two points.

Integrated into the design of the system console 60 are means of visually or graphically communicating results. These means include a cathode ray tube (CRT) 65 and a graphic paper printer 84C to produce a hard copy of any image appearing on the face of the CRT 65. Also included in the scanner console 60 is a "minifloppy" magnetic disc system 75D. This facilitates the storage of clinical results on a large number of patients combined with patient history information. Acquisition, retrieval and management of all data is facilitated by fingertip control at the console keyboard 80.

Before proceeding with a discussion of the configuration and operation of the ultrasonic scanning system it is appropriate to discuss the features of the scanner head 10 and the mechanical system 30 which supports and transports the head. The concept of the scanner head 10 is perhaps best illustrated by FIGS. 3 and 5a. One unique feature of this system is that the individual transducer elements 12 are affixed to plungers 15 which have one degree of freedom of movement, but may move independently of one another. Each plunger/transducer combination is spring loaded within a common housing 16 to all plungers 15 such that when the assembly 10 is pressed against the back of a patient each transducer 12 provides positive compression against the skin 11. As the scanner head 10 is then moved over a complex plane of body curvature such as the human back each transducer 12 independently tracks the curvature such that positive acoustic coupling is maintained for each active element in the scanner head 10.

An alternative embodiment of the scanner head is shown in FIGS. 6a and 6b and has been described above. This embodiment has an additional structural degree of freedom of movement that allows it to adjust to the curvature of the back so that the faces of the transducer elements, such as 149, are tangent to the surface of the back 11.

As the transport system is brought to the patient's back such that landmarks X and Y are located and are contacting landmark probes 141A and 141B, transducer shoes 148 seek positive skin contact as before because of spring loading pressure on plunger 143 relative to housing 142C. In position No. 1 of FIG. 8a, assume roller 146B contacts the patient's back before roller 146A. Because of positive pressure caused by springs 147C and 147D, the transducer array 142 rotates counterclockwise about roller axle 146D. Simultaneously housing 142B rotates about pivots 145A and 145B until roller 146A is in positive contact with patient's back 11. The system is now in equilibrium with the transducer element face 149 parallel to line aa'. Because of the geometry of construction, line aa' is a very close approximation, if not exact, tangent at point "A" to the average curvature of the back 11 between rollers 146A and 146B.

In operation, then, as the scanner head 9 descends (preferably under motor power) along transport rails 140A and 140B, rollers 146A and 146B are forced to maintain positive skin contact with the patient's back 11. Angle φ, in general, varies to maintain the tangential curve tracking situation. Position No. 2 simply depicts the position of the system as the head 9 nears the end of its downward movement. Here the point of curve tangency is at point "B".

The linear position transducer 20 shown in FIG. 5b may be used in combination with either of the plunger systems described above. In those embodiments which employ linear position transducer 20, each such linear position transducer 20 is an integral part of each independent plunger. The output of the linear transducer is used to make correction in the computed range value as shall be described below.

Also shown in FIG. 2 is the detail of the transducer shoes 14 which are contoured assemblies into which the transducer elements 12 fit. The shoes 14 prevent the conventional transducer elements from gouging into the skin 11 of the patient as the scanner head 10 moves. The shoes 14 greatly alleviate this discomfort.

The mechanical transport system for moving the scanner head down the back is illustrated in FIGS. 2, 3 and 4. Note that the system implemented employs a servo motor 41 and gear reduction (within motor housing) to turn a set of cable drums 47A and 47B. The drums cause steel cables 48A and 48B to move. The scanner head 10 is attached to the cables 33A and 33B such that movement of the cables causes the scanner head 10 to slide either up or down the transport side rails 33A and 33B at a rate determined by the speed of motor 41.

A number of alternative transporters for the scanner head may be employed, for example a servo motor and gear drive which rotate a long screw shaft positioned midway between the transport side rails 33A and 33B. The screw shaft may be attached via a mating threaded collar to the rear of the scanner head 10. Thus, rotation of the screw shaft would facilitate movement of the scanner head along the side rails.

Still another alternative method of scanner head transportation is to mount a set of wheels on the transducer array assembly. The transducer array 70 and wheel assembly would be pressed against the back and moved manually down the back. The wheels would serve to convert angular rotation of the wheels to linear distance traveled down the back by the transducer array.

A block diagram of the scanning system is shown in FIG. 7. As discussed above, the system is microprocessor-based. The specific microprocessing and display system is shown in more detail in FIG. 8i. The console electronics may be mounted on nine printed circuit boards which insert into console 60 from the rear.

The central processing unit chosen was the Intel 8085 processor chip incorporated on an Intel ISBC 80/30 single-board computer. This in itself is a relatively powerful 8-bit microcomputing system containing 4K of read only memory (ROM) and 16K of random access memory (RAM). In addition, an Intel ISBC 116 memory board was included to increase the RAM by 16K. In the discussion which follows concerning the system operation, it is emphasized that all activity is under software control. Software design was, therefore, an intimate part of the overall system design. Broadly speaking, the software may be categorized as operational software or data processing software. Operational software includes all the necessary computer instructions required to control the scanning operation, acquire necessary raw echo data, and store this data in memory. Data processing software includes those computer programs which operate on the raw data to provide numerical and/or graphical characterization of the results. Reference to commands or instructions implies computer instructions implemented via the microprocessor.

The graphics or display system is configured in such a manner that the face of the 12 inch CRT 65 may be characterized as a dot matrix of $512 \times 512$ discrete dots each of which may be selectively either lighted or not lighted. This is particularly well suited to this application because data in matrix form may set up so that it may be mapped into a corresponding field on the CRT 65. In addition, the system provides the capability of eight-level grey scale in the image, i.e. each dot, when turned on, may be set at one of seven levels of light intensity. This was facilitated by interfacing commercially available Matrox MSBC 512 graphics printed circuit cards 84A with the Intel ISBC 80/30 system, as indicated in FIG. 8i. In addition, a Matrox BSBC 2480 board 84B was added for the generation and display of alphanumeric symbols. The system also incorporates an Axiom Ex-850 Video Printer 84C so that any image on the face of the CRT 65 may be turned into hard copy at the touch of a button. This particular video printer, however, will not reproduce intermediate levels of grey-scale.

Under processor control any one or any combination of the ultrasonic transducers in the array 70 may be selectively chosen to emit or receive sound energy. In the Fundamental mode of operation, however, each transducer in sequence is activated to first emit a short pulse of sound energy and then to receive or listen for returning echoes.

The scanning system may be also operated in a data acquisition mode called Multireceiver. This mode is designed to enhance the probability of capturing target echoes and it will be discussed later.

In the Fundamental mode a set of commands from the microprocessor presents a transducer transmitter selection code to the one of sixteen selector 72 as well as received signal multiplexer 73 (FIG. 7). For example, transducer $T_0$ is designated as the transmitting transducer via appropriate control signals to the one of sixteen selector 72. Transducer $T_0$ is then fired by transducer drive circuit 71D (FIG. 8C). Immediately thereafter a transducer receiver selection code is input to the multiplexer 73 to designate which transducer or transducers will listen for echoes. In the Fundamental mode $T_0$ would be designated as the receiver.

Simultaneously with the launching of a sound wave, a set of one or more range counters 82 are started. The rate of count is controlled by the microprocessor system clock and is approximately 1.2 MHz in the embodiment described. As echoes are received by the designated receiving transducer, this reflected sound energy is converted to a very low level analog voltage with a fundamental frequency equal to the fundamental frequency of the launched sound wave (2.25 MHz). After passing through the multiplexer and receiver blocks 73, this analog echo signal is amplified by a factor of 2 to 5 by the linear preamplifier 74.

The preamplifier is followed by a custom-designed nonlinear time-gain amplifier 76 which has a number of controllable parameters. The details of this circuit and its features will be explained further below. The time-gain amplifier 76 provides a signal gain which increases with time. The time reference for the initiation of this specialized amplification process is keyed from the command to launch a sound wave. As an initial sound wave propagates away from the transducer of origin through the body tissue, it dissipates or is attenuated. Likewise, any reflected energy (echo) is similarly attenuated in the return path. Therefore, since we wish to discriminate echoes on the basis of amplitude, the philosophy in designing the time-gain amplifier is to compensate for sound energy losses in tissue with respect to time.

The gain compensated echo signal is now fed to the echo discriminator block 83. On the front end of the echo discriminator is an RF detector or full wave envelope detector (FIG. 8d.2). The purpose of this detector is to remove the high frequency (2.25 MHz fundamental frequency plus harmonics) components from the signal. This results in a signal which is the envelope of the echo signal. This echo profile or echo pattern, therefore, in general, consists of a series of pulses, the amplitude and time position of which contain information about the various tissue interfaces and the distance or depth in the overall tissue aggregate at which such interfaces reside.

Following envelope detection the echo profile signal is fed into a voltage comparator circuit (FIG. 8d.2). The nature of the comparator circuit is such that when and only when an input signal exceeds a selected voltage amplitude, the comparator outputs a well-defined voltage pulse. The output of the comparator provides a "stop" signal for the range counter (FIG. 8e).

Therefore, in the Fundamental mode of operation, the most rudimentary echo detection algorithm is designed such that the first echo in time to exceed a preselected amplitude is detected and used to stop the range counter 82 (FIG. 8e).

The relative position of the scanner head 10 with respect to the support 30 is monitored by a position transducer 79 (potentiometer 50 connected to the motor drive system) which generates a DC voltage level proportional to distance of travel of the scanner head 10. This DC voltage is converted to a digital binary word by the position A/D converter 81 shown in FIG. 8b.

After sufficient time has elapsed (about 200 $\mu$s for 100 mm of range) for the range counter or counters 82 to contain an appropriate count, the position of the scanner head is determined by the processor. Immediately following this, the data in the range counter 82 is read. The range count which resides as the number of counts per unit of system clock time is used to calculate the "range" or distance from the transducer face to the tissue interface responsible for generating the echo. This is accomplished by the equation: Range=round trip distance/2, or Range=(velocity of sound in tissue)×(time to receive echo/2). Using a range counter clock frequency of 1.23 MHz and an average velocity of sound in tissue of 1540 m/s, this equation reduces to Range=0.63×COUNT, where COUNT is the number in the range counter.

In the discussion below the notation Y(J)·X(I) shall designate a memory matrix allocated to store "raw" range data. Raw will mean unsmoothed or otherwise unprocessed data. As an example, a range calculation of 30 mm derived from the echoes detected by T$_0$ transducer at the uppermost position of the scanner head would be entered in the raw data memory matrix as Y(O)·X(O)=30.

The process described above is repeated under microprocessor control until the scanner head 10 has descended through all the "J" increments of interest. The raw range data matrix is therefore filled from the first Y(O)·X(O) element to the last Y(479)·X(15) element following the example set forth. It should be appreciated that the entire process of sound transmission, reception or retransmission, echo discrimination, and data storage occurs very rapidly relative to the rate of movement of the scanner head 10. Thus, the scanner head does not have to start and stop, but rather moves continuously down the back once the scan is initiated. The processing of this stored data is described later.

An alternative embodiment of the invention includes two range counters 82. In this embodiment a detection algorithm may be mechanized in which two range values may be ascribed to the first two echoes to exceed prescribed thresholds. Such an algorithm is useful as a bone edge detector.

As described, range counter No. 1 (FIG. 8e) begins counting when a sound wave is launched from a transducer element. The counter is stopped by a signal at input YY. The final count in range counter No. 1 is indicative of the range or distance from the transducer to the first tissue structure of interest nearest the transducer. After the microprocessor 75 reads range counter No. 1, the microprocessor resets this counter by appropriate signals on J1-20 (reset line) and J1-24 (strobe line).

The second range counting system (FIG. 8f) and specifically counter 82I also begins counting when a sound wave is launched from a transducer element. If a second more distant tissue structure of interest is detected, counter 82I is stopped by the presence of a stop signal on YY of FIG. 8f. Counter 82I will not be stopped by the first detected echo, because line XX will not go high (logical "1") to enable a stop signal to be recognized by 82I until a first echo occurs. The contents of 82I thus represent the range to the second tissue interface of interest, and it may be read by microprocessor 75. Subsequently, range counter No. 2 is reset after being read via lines J1-20 and J1-24. In the event a second echo is not detected, counter 82I will overflow and thus automatically reset.

Another alternative embodiment includes linear position transducer 20 (FIG. 5b) which provides the position of each transducer, such as 28, along the "Z" direction, that is a direction perpendicular to the field or plane of scan defined by the "X" and "Y" coordinates referred to above. This position is fed into the microprocessor to refine the range values or in order to determine the range values with respect to an absolute plane, rather than in respect to the relative plane of the back. Such absolute range values may enhance the visual reconstruction of the dorsal skeletal structure and thus improve the resolution of the scoliotic curve characterization.

Shown in FIG. 7 is a high-speed A/D converter and memory buffer system 85 which is connected by dashed lines to the main scanner system. This part of the system is primarily for research purposes and may be brought "on line" as an option. The circuitry for this part of the system is shown in FIGS. 8g.1, 8g.2, 8h.1 and 8h.2 and the characteristics are described below. Since echo patterns are extremely transient in nature, the high-speed A/D converter and memory buffer 85 provide an ultrahigh-speed means of examining a designated echo pattern. When in use the memory buffer is always saving a prescribed number of scan lines or J lines of continuous echo amplitude data. For example, if the standard echo detection algorithm provides questionable data in some portion of the field scan, the appropriate contents of the memory buffer system may be interrogated under software control to recreate the analog echo pattern in this specific region of interest. The validity of the echo detection algorithm in this region of question may then be examined.

A smooth planar surface tends to reflect a sound beam according to Snell's law (i.e., angle of incidence equals angle of reflection). Thus, in such a simple case, the maximum "signal strength" of the echo pattern is obtained when the incident beam is perpendicular to the reflecting interface. In most practical cases, and in particular, with the irregular surface geometry of the bony structure of the ribs and spine, this ideal condition does not exist for all components of the target. An incident sound beam, although it can be focused, cannot be made infinitely narrow and, therefore, at least some minimal energy will return to the transmitting transducer unless the target surface has an extremely oblique angle relative to the face of the transducer. The system, when operated in the Fundamental mode of data acquisition, relies on the high sensitivity of the receiving transducer 12 and the gain characteristics of the echo amplifiers 74 and 76 to capture at least a portion of the reflected energy contained in an echo from bone.

To enhance the probability of receiving echoes from bone returning not along the longitudinal axis of the sending transducer, the Multireceiver mode of operation was devised. The Multireceiver algorithm is designed to operate in conjunction with a row of transducers as shown in FIGS. 3 and 5a.

In the basic Multireceiver algorithm, a transducer (e.g., $T_2$ of FIG. 5a) launches a sound wave and then the same transducer $T_2$ listens for echoes. If no echoes are received, $T_2$ refires, only adjacent transducer $T_1$ now listens. If still no echo, $T_2$ refires and the other adjacent transducer $T_3$ listens. Following this procedure, the next transducer in normal sequence (namely $T_3$) fires and listens. If no echo, $T_3$ refires; $T_2$ listens. If no echo, $T_3$ refires, $T_4$ listens and so on. Because the adjacent transducer elements are intentionally located close together, very little error in calculated range values occur whether the launching transducer receives an echo or an adjacent transducer receives an echo. Nevertheless, errors in range values may be minimized by making fundamental trigonometric calculations which compensate for the displacement between the transmitting and receiving transducers.

The main purpose of the echo processing electronic circuits which are under control of the microprocessor is to detect valid ultrasonic echoes and to calculate the distance from the transducer to the structure that reflected the incident ultrasonic pressure wave.

In general, echoes will occur whenever the transmitted ultrasound encounters a bone and muscle (or soft tissue) interface, a muscle and lung interface, or even a skin and muscle interface. The size of the echo depends on several factors; the characteristics of sound (velocity and attenuation) in each medium and the angle of incidence of the sound and the interface.

The scanner head electronics is shown within the dashed lines of FIG. 7. The sixteen transducers (shown in FIGS. 2, 4 and 5a) are mounted side-by-side, making up a horizontal array approximately six inches wide.

Each transducer has a separate drive circuit 71D (FIG. 8c) which can be addressed by the microprocessor in various patterns; the usual pattern is to begin at the left and sequentially activate each transducer. The drive circuits supply a short, high voltage (200 to 500 volts) pulse to the transducers. This causes an ultrasonic pressure wave to travel out from the surface of the transducer. This pressure wave travels through body tissue at a typical velocity of 1540 m/sec and the tissue attenuates it by an average of 2 db/cm.

Echoes produced by bone/tissue interfaces return to the transducer surface and cause an electrical response in proportion to the magnitude of the echo as has been previously explained.

Immediately after the transducer is activated, it is connected to a receiver and amplifier circuit (FIG. 8c), such that any returning echoes can be amplified and processed further.

The linear preamplifier 74 located on the scanner head 10 provides only a small amount of gain, but does provide the necessary drive to send the signal back to the main electrodes package 60.

In the circuit of FIG. 8d.1 the nonlinear time dependent gain amplifier 76 includes a dual gate field effect transistor (FET) 76B. One gate, 76E of the FET controls the gain characteristics and the other gate 76F is the echo signal input. The SIGNAL AMP (back panel adjustment) control 76G is connected to the echo signal input gate 76F. By keeping the control gate 76E at a negative potential, the signal on the other gate does not appear at the output of the FET. As the voltage level on the control gate 76E increases, the gain of the FET increases until the maximum gain is reached. By changing the voltage level on the control gate 76E of the FET it is possible to have a time of zero gain and a time when the gain is increasing linearly towards the maximum gain. Ideally, the gain would never be less than one, however, because of transducer ringing, it is necessary to have zero gain for several microseconds following the activation of the transducer. By controlling the time until maximum gain is reached corresponding to a depth of one to five centimeters the attenuation of the signal by tissue can be compensated.

Of the seven external back panel adjustments, four are related to the control gate signal. These four are RAMP OFFSET 76H, DELAY 76I, SEGMENT 1 76J, and SEGMENT 2 76K. These potentiometers are located in the circuit of FIG. 12d. The RAMP OFFSET 76H adjusts the negative potential on the control gate 76E. The DELAY 76I adjusts the time at which the amplifying process begins relative to the launching time of a sound wave (time zero). The profile of the time-gain characteristic may be regarded as having three segments. The slopes of the first and second segments are determined by the settings on the SEGMENT 1 76J and SEGMENT 2 76K controls respectively. The gain of third segment is inherently the maximum gain available from the amplifier. The WINDOW (bank panel adjustment) control 76L sets the maximum allowable time for amplification.

The RF detector (FIG. 8d.2) full wave rectifies the echo and applies this rectified signal to the comparator also shown in FIG. 8d.2. The comparator has an adjustable threshold setting 83D called DETECTOR THRESHOLD (back panel adjustment). Thus, only echoes above the threshold are detected.

When an echo is detected, the range counter of FIG. 8e is stopped. The count that has accumulated corresponds to the range (or depth) of the structure that produced the echo. The resolution of the range counter is in the preferred embodiment 0.6 mm.

A second counter which is indicated in FIG. 8f can also be started when a transducer is fired. This gives the capability of calculating the range for the first two echoes that exceed the comparator threshold.

Not every transmission produces an echo. There are many possible reasons for not getting an echo large enough to trigger the comparator. The target may have been at such an angle to the incident sound wave that the echo may not return directly to the detector, or there may not have been a target within the maximum range of 150 mm. The application of the Multireceiver mode in alleviating these problems has been discussed.

In order to examine the analog echo signal in the event that echoes are not detected, a high-speed analog-to-digital (A/D) converter (FIGS. 8g.1, 8g.2, 8h.1 and 8h.2) can be brought on line under software control. The A/D converter 85B employed is a TRW model TDC1007PCB module. The 8-bit A/D converter output goes to an array of shift registers, such as 85C, that can hold 1024 8-bit conversions of the analog echo signal. The conversions are made at a 10 MHz rate; therefore, 102.4 microseconds of data can be held in the shift registers. The data can then be automatically clocked out of the shift registers at a slower rate providing a data expansion capability.

Alternatively, the data in the shift registers can be stored in the microprocessor memory 75A and 75B. Each 100 microseconds of data would require 1K of memory.

Examination of this data allows a more desirable detector level setting or gives insight into a more intelligent nonlinear gain curve characteristic. To enhance the probability of detecting more echoes the detector level may be adjusted dynamically. For example, if an echo is not detected after a transmission, the detector sensitivity may be increased and a second transmission made. If an echo is still not detected, the iterative process of detector level shifting and retransmission could be continued.

The position A/D converter 81 (FIG. 7b) provides a signal proportional to the vertical position of the scanning array. When the appropriate vertical distance has been scanned, the microprocessor 75 will stop activating the transducers 70 and inform the operator that the scan is complete.

The range data from each of the echoes received during a scan are stored in the microprocessor's memory 75A and 78B. This information is available for future processing and is used to generate a display that shows the spine and ribs.

DATA ACQUISITION AND PROCESSING

Figure 9:
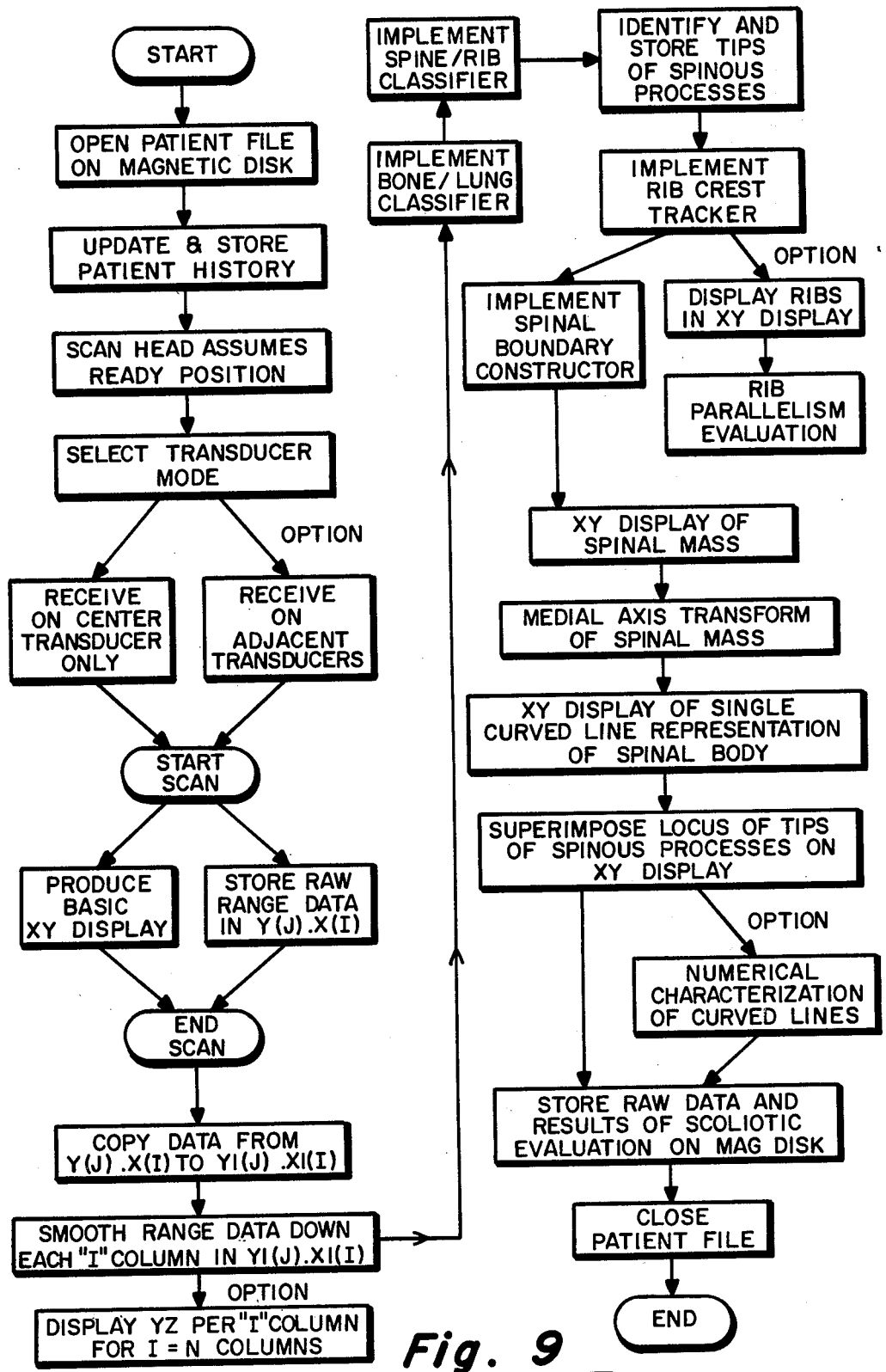
FIG. 9 shows a flow diagram for the preferred embodiment of the method according to the invention indicating the progression of scanner startup, data acquisition and data processing.

FIG. 9 is a flow diagram indicating the progression of scanner startup, data acquisition, and data processing. Certain optional decisions selected via the keyboard 80 are indicated which, in general, yield intermediate displays and supplemental results on route to the final characterization of the curvature of the patient's spine.

After the instrument is powered up, the patient's name and/or a file number is entered. For a returning patient, a summary of the results of the previous evaluation is read from floppy disc memory 75D and presented on the CRT 65 of the console 60. For a new patient, a new file on magnetic disc 75D would be created and the relevant aspects of the patient's history is entered. When the patient is prepared for the scan, a command at the keyboard 80 causes the scanner head 10 to automatically seek the "ready" position along the transport rails 33A and 33B. Subsequently, the mode in which the transducers 12 are to operate is selected. The scanner head 10 is then pressed against the patient's back such that the individual transducer elements 12 are in positive compression against the patient's skin 11. The transport system's reference points, cervical 31 and sacral 32, are correctly aligned on the patient's back 11 by palpation.

A keyboard command, or alternatively, momentary depression of a remote start button 64 (FIG. 1) mounted on the transport system 30 initiates the scanning procedure. As the scan is progressing under software control, a real time display is presented on the CRT 65 of the system console 60. This shall be known as the Basic XY display. A portion of the 512×512 dot matrix CRT field is selected to be a proportioned scale replica of the XY field of scan on the back 11 of the patient. Therefore, a field of 16 pixels by 480 pixels represents the back 11 of the patient. At the beginning of the scan this CRT field is darkened. The Y(J)·X(I) memory matrix which is used to drive the CRT pixel field is initialized with all elements set to range values of 150 mm. A range value of 150 mm is arbitrarily chosen as the maximum range value of any relevance for our purposes. Therefore, the "background" value for this imaging becomes 150 mm. As the scan proceeds, each calculated range value is tested against a criteria of being between (but not equal to) 0 mm and 150 mm. If this condition is met, the memory value of 150 is replaced with the new range value and the corresponding pixel on the screen is lighted.

In practice the rate of travel of the scanner head 10 down the back 11 of the patient is very slow compared to the rate of firing of the transducers 12. A typical scan requires a half minute to a minute to complete, whereas the firing and listening sequence of 16 transducers at a particular J level may be completed in 30 ms to 100 ms. It was determined experimentally that it was desirable to have each transducer 12 interrogate the same elemental region of the field of scan more than once so as to enhance the probability that relevant echoes would be received. Therefore, the system is adaptable so that there are multiple opportunities for acquisition of echo data and hence the replacement of the initialized range values (150 mm). A software option is discussed below for averaging of multiple attempts or the presentation and display of the contribution to end results from multiple attempts. Once the background value of 150 mm is replaced, it was found desirable to "lock-out" further attempts to change the range value during the same scan.

The echo signal amplifiers 74 and 76 and detection system 83 were designed and adjusted so that there is a high probability of triggering the discriminator 83 and hence producing a valid range value at each discrete element in the field of scan even though the transmitted sound wave does not encounter bone. This occurs because a large portion of the scan field is in the thoracic region. In this region the lungs and plural sac of the lungs are in close proximity to the ribs. In viewing the patient from the back, the ventral aspect of the ribs is in apposition with the plural sac. Experimentally, it was found that significantly strong echoes are returned from this plural tissue interface between the ribs. Importantly, the average range values returned in the intercostal spaces are larger than those range values returned from the dorsal aspect of the ribs. The average difference is the thickness of a rib (5 mm to 10 mm), and this formulated the basis of the software which extracts rib from lung, i.e., the Bone/Lung Classifier.

Upon completion of the scanning operation, the Y(J)·X(I) data matrix is filled with raw data. This data is then copied into the $Y_1(J) \cdot X_1(I)$ data matrix. The data in the $Y_1(J) \cdot X_1(I)$ matrix is processed and changed while the Y(J)·X(I) matrix preserves the raw data which is eventually transferred to magnetic disc storage 75D under the patient's raw data file. Next, the $Y_1(J) \cdot X_1(I)$ data is subjected to a routine smoothing operation. The data is smoothed down each "I" column. This data may then be processed and analyzed via software as indicated in FIG. 8 to generate a display that shows the spine and ribs.

The data processing is concluded as indicated in FIG. 8 by the storage of the results of the scoliotic examination on the patient's permanent file residing on magnetic disc 75D. The file is then closed. The system may then be initialized for the next examination.

There has been described a novel system for ultrasound scanning which provides apparatus for ultrasonic imaging of the human back, and is particularly suited for detecting the spinal curvature that is indicative of scoliosis. While the invention has been described in connection with a single preferred embodiment for the entire system and a number of alternative embodiments for particular parts of the system, one skilled in the art will appreciate that numerous other embodiments of the entire system and further alternative embodiments of various parts of the system and departures from the particular embodiments and alternative embodiments shown may be made without departing from the inventive concepts. For example, a wide variety of different scanner heads, scanner head transport systems, and computer control and processing systems and display systems and software may be used while still employing the inventive concepts. It is therefore to be understood that, within the scope of the appended claims, the invention may be practiced other than as has been specifically described.

What is claimed is:

1. An ultrasound imaging system for scanning the skeletal structure of the human back comprising:
    frame means for positioning relative to the back and for defining an axis which crosses over the spine at at least two points;
    an array of ultrasound transducers moveably mounted on the frame for movement along the axis in contact with the human back, each ultrasound transducer of the array having means for generating an ultrasound signal, for receiving an ultrasound signal, and for producing an electrical signal representative of the received ultrasound signal;
    means for producing a position signal representative of the position of the array along the axis;
    means responsive to the electrical signals for providing a range signal representative of the distance from the transducer to objects within the body interacting with the received ultrasound signal; and
    means responsive to the range signal and the position signal for producing an output representative of spinal curvature of the human body relative to the axis.

2. The ultrasound imaging system of claim 1 further comprising:
    means for moving the array of ultrasound transducers along the axis.

3. The ultrasound imaging system of claim 2 wherein:
    the means for moving includes a motor for moving the array in response to control signals; and
    a control system for generating control signals and transmitting them to the motor, the control signals being indicative of rate of movement from one reference point to another.

4. The ultrasound imaging system of claim 1 wherein the frame further comprises:
    means to allow transducers of the array to rock so as to remain tangent to the surface of the back while scanning the skeletal system of the back.

* * * * *

UNITED STATES PATENT AND TRADEMARK OFFICE
CERTIFICATE OF CORRECTION

PATENT NO. : 4,457,311
DATED : 3 July 1984
INVENTOR(S) : Paul D. Sorenson, Dale A. Dickson It is certified that error appears in the above-identified patent and that said Letters Patent are hereby corrected as shown below:

Column 5, line 9, "4800" should be --4080--;

Column 7, line 30, "if" should be --it--;

Column 10, line 20, "by he" should be --by the--;

Column 11, line 53, "division" should be --Division--;

Column 13, line 11, "or" should be --of--;

Column 15, line 64, "BSBC" should be --MSBC--;

Column 19, line 63, "electrodes" should be --electronics--;

Column 21, line 25, "78B" should be --75B--.

Signed and Sealed this

First Day of January 1985

[SEAL]

Attest:

GERALD J. MOSSINGHOFF

Attesting Officer

Commissioner of Patents and Trademarks